United States Patent
Donnet

(10) Patent No.: US 10,254,242 B2
(45) Date of Patent: Apr. 9, 2019

(54) METHODS, SYSTEMS, AND COMPUTER-READABLE MEDIA FOR COMPRESSION OF SEQUENCING DATA

(71) Applicant: Life Technologies Corporation, Carlsbad, CA (US)

(72) Inventor: Benjamin Donnet, Wynnum (AU)

(73) Assignee: Life Technologies Corporation, Carlsbad, CA (US)

(*) Notice: Subject to any disclaimer, the term of this patent is extended or adjusted under 35 U.S.C. 154(b) by 530 days.

(21) Appl. No.: 14/729,640

(22) Filed: Jun. 3, 2015

(65) Prior Publication Data

US 2015/0355138 A1 Dec. 10, 2015

Related U.S. Application Data

(60) Provisional application No. 62/007,435, filed on Jun. 4, 2014.

(51) Int. Cl.
*G01N 27/414* (2006.01)

(52) U.S. Cl.
CPC .................. *G01N 27/414* (2013.01)

(58) Field of Classification Search
CPC ..... H03M 7/30; H03M 7/3062; G01N 27/414
See application file for complete search history.

(56) References Cited

U.S. PATENT DOCUMENTS

| | | | |
|---|---|---|---|
| 7,233,870 B1 * | 6/2007 | Dalrymple | G06K 9/0051 702/76 |
| 7,834,795 B1 * | 11/2010 | Dudgeon | G06K 9/6289 341/155 |
| 7,948,015 B2 | 5/2011 | Rothberg et al. | |
| 2007/0188749 A1 | 8/2007 | Brady et al. | |
| 2009/0026082 A1 | 1/2009 | Rothberg et al. | |

(Continued)

FOREIGN PATENT DOCUMENTS

WO 02/33558 4/2002

OTHER PUBLICATIONS

Bartholomä, R. et al., "Implementing Signal Processing Algorithms on FPGAs", *University of Applied Sciences Pforzheim*, Germany http://citeseerx.ist.psu.edu/viewdoc/download?doi=10.1.1.130.8731 &rep1&type=pdf, 4 pgs.

(Continued)

*Primary Examiner* — Kyle R Quigley
(74) *Attorney, Agent, or Firm* — Carolyn Koenig

(57) ABSTRACT

Methods, systems, and computer-readable media are disclosed for compression of sequencing data. One method includes receiving waveform data associated with a chemical event occurring on a sensor array, the waveform data including a plurality of time-based waveforms of a corresponding plurality of locations of the sensor array; converting, by at least one processor, each time-based waveform of the waveform data into a frequency-domain spectrum; generating, by the at least one processor, a key frame based on a plurality of the frequency-domain spectrums; calculating, by the at least one processor, for each of the frequency-domain spectrums, a difference between the frequency-domain spectrum and the key frame; and encoding, by the at least one processor, each calculated difference between the frequency-domain spectrum and the key frame.

20 Claims, 23 Drawing Sheets

(56) References Cited

U.S. PATENT DOCUMENTS

| | | |
|---|---|---|
| 2009/0083809 A1* | 3/2009 | Hayashi ................. H04N 5/783 |
| | | 725/88 |
| 2010/0137143 A1 | 6/2010 | Rothberg et al. |
| 2010/0282617 A1 | 11/2010 | Rothberg et al. |
| 2011/0263463 A1* | 10/2011 | Rothberg ............. C12Q 1/6874 |
| | | 506/39 |
| 2012/0109598 A1 | 5/2012 | Davey et al. |
| 2013/0060482 A1 | 3/2013 | Sikora et al. |
| 2013/0090860 A1 | 4/2013 | Sikora et al. |
| 2014/0093881 A1 | 4/2014 | Sugnet et al. |

OTHER PUBLICATIONS

Gallagher, S, "Mapping DSP Algorithms Into FPGAs", *Xilinx, Inc.*; http://www.ieee.li/pdf/viewgraphs/mapping_dsp_algorithms_into_fpgas.pdf, 35 pgs.

Martucci, S, "Symmetric Convolution and the Discrete Sine and Cosine Transforms", *IEEE Transactions on Signal Processing*, vol. 42, No. 5, 1994, 1038-1051.

Narasimha, M et al., "On the Computation of the Discrete Cosine Transform", *IEEE Transactions on Communications*, vol. 26, No. 6, 1978, 934-936.

PCT/US2015/033986, ,International Search Report and Written Opinion dated Sep. 3, 2015, 9 Pages.

Woods, R. et al., "FPGA-based Implementation of Signal Processing Systems", *John Wiley & Sons*, ISBN 978-0-470-03009-7, 2008, 388 pgs.

EP 15802502.3, Extended European Search Report dated Jan. 5, 2018, 8 pp.

\* cited by examiner

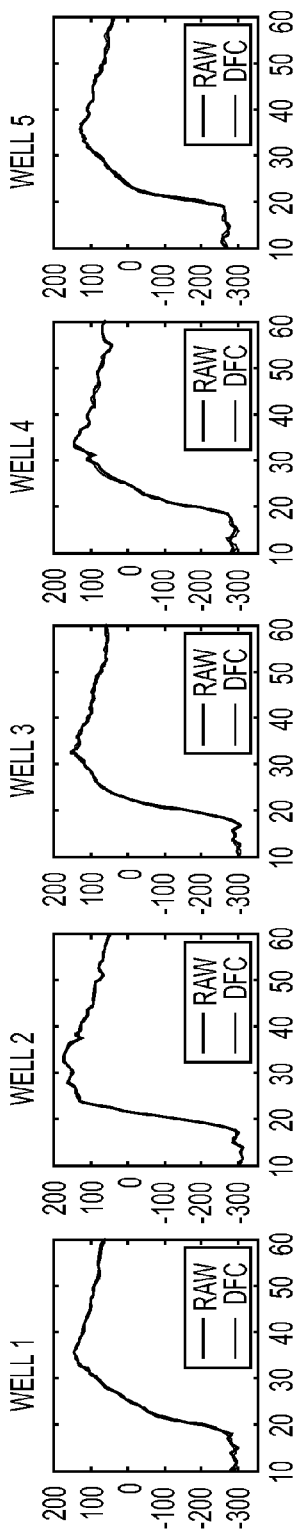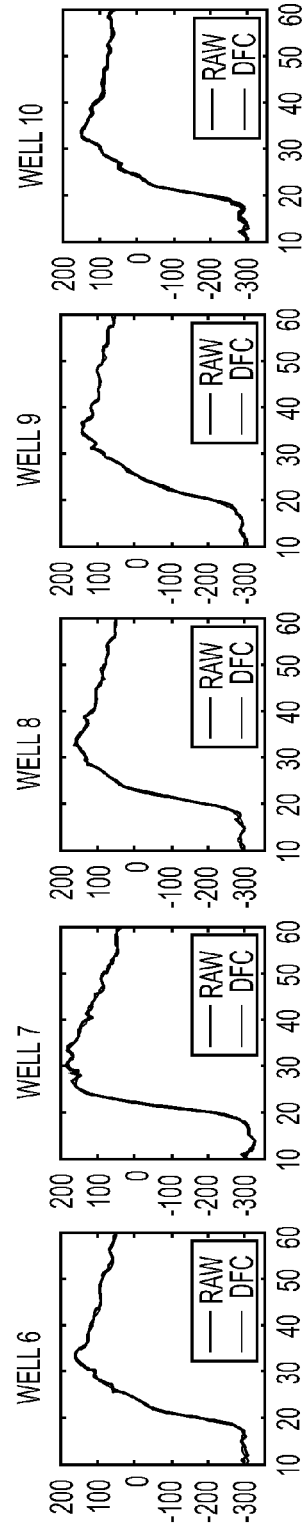

METHODS, SYSTEMS, AND COMPUTER-READABLE MEDIA FOR COMPRESSION OF SEQUENCING DATA

CROSS-REFERENCE TO RELATED APPLICATIONS

This application claims priority under 35 U.S.C. § 119(e) to U.S. Provisional Application No. 62/007,435, filed Jun. 4, 2014, entitled "Methods, Systems, and Computer-Readable Media for Compression of Sequencing Data," and the contents of the foregoing application are incorporated herein by reference in their entirety.

COMPUTER PROGRAM LISTING APPENDIX

This application contains a Computer Program Listing Appendix, which has been submitted in ASCII format via EFS-Web and is hereby incorporated by reference in its entirety. Said ASCII copy is named LT00869_Computer_Program_Listing.txt, was created on Dec. 11, 2018, and is 21,951 bytes in size.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE DISCLOSURE

The present disclosure is directed generally to inventive methods, systems, and computer-readable media relating to compression of sequencing data obtained by detection and measurement of one or more analytes including analytes associated with or resulting from a nucleic acid synthesis reaction.

BACKGROUND

Electronic devices and components have found numerous applications in life sciences, including chemistry and biology, especially for detection and measurement of various chemical and biological reactions and identification, detection, and measurement of various compounds. One such electronic device is referred to as an ion-sensitive field effect transistor ("ISFET"). ISFETs facilitate measurement of a hydrogen ion concentration of a solution (commonly denoted as "pH").

More specifically, an ISFET is an impedance transformation device that operates in a manner similar to that of a metal oxide semiconductor field effect transistor ("MOSFET"), and is particularly configured to selectively measure ion activity in a solution (e.g., hydrogen ions in the solution are the "analytes").

With faster sampling data rates and higher densities of sensor arrays of ISFETs, large amounts of data may be produced. It is thus desirable to reduce memory consumption while maintaining the quality of data. A goal of at least certain methods discussed in detail below, among others, is to accurately capture data associated with a biological/chemical event, while reducing noise associated with the data. This goal may be achieved by implementing compression techniques described below. As a result, the amount of data stored may be reduced.

SUMMARY OF THE DISCLOSURE

Embodiments disclose methods, systems, and computer-readable media for compression of sequencing data.

According to certain embodiments, computer-implemented methods are disclosed for compression of sequencing data. One method includes: receiving waveform data associated with a chemical event occurring on a sensor array, the waveform data including a plurality of time-based waveforms of a corresponding plurality of locations of the sensor array; converting, by at least one processor, each time-based waveform of the waveform data into a frequency-domain spectrum; generating, by the at least one processor, a key frame based on a plurality of the frequency-domain spectrums; calculating, by the at least one processor, for each of the frequency-domain spectrums, a difference between the frequency-domain spectrum and the key frame; and encoding, by the at least one processor, each calculated difference between the frequency-domain spectrum and the key frame.

According to certain embodiments, systems are disclosed for compression of sequencing data. One system includes a data storage device that stores instructions for compression of sequencing data; and a processor configured to execute the instructions to perform a method including: receiving waveform data associated with a chemical event occurring on a sensor array, the waveform data including a plurality of time-based waveforms of a corresponding plurality of locations of the sensor array; converting each time-based waveform of the waveform data into a frequency-domain spectrum; generating a key frame based on a plurality of the frequency-domain spectrums; calculating, for each of the frequency-domain spectrums, a difference between the frequency-domain spectrum and the key frame; and encoding each calculated difference between the frequency-domain spectrum and the key frame.

According to certain embodiments, non-transitory computer readable media are disclosed that store instructions that, when executed by a computer, cause the computer to perform a method compression of sequencing data. One computer-readable medium includes the method of: receiving waveform data associated with a chemical event occurring on a sensor array, the waveform data including a plurality of time-based waveforms of a corresponding plurality of locations of the sensor array; converting, by at least one processor, each time-based waveform of the waveform data into a frequency-domain spectrum; generating, by the at least one processor, a key frame based on a plurality of the frequency-domain spectrums; calculating, by the at least one processor, for each of the frequency-domain spectrums, a difference between the frequency-domain spectrum and the key frame; and encoding, by the at least one processor, each calculated difference between the frequency-domain spectrum and the key frame.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the scope of disclosed embodiments, as set forth by the claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 17A-17J depict exemplary raw time-domain waves and reconstructed time-domain waveforms of various wells of a sensor array, according embodiments of the present disclosure;

DETAILED DESCRIPTION OF EMBODIMENTS

Exemplary embodiments of the present disclosure relate in part to the use of large arrays of chemically sensitive field effect transistors ("chemFETs"), and more particularly to ion-sensitive field effect transistors ("ISFETs"), which monitor reactions, including for example deoxyribonucleic acid (e.g., DNA) sequencing reactions, based on monitoring analytes present, generated, and/or used during a reaction.

Arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Accordingly, at least certain embodiments of the systems, methods, and computer-readable media discussed herein provide uses for chemFET arrays that involve detection of analytes in solution and/or detection of change in charge bound to the chemFET surface.

Figure 1:
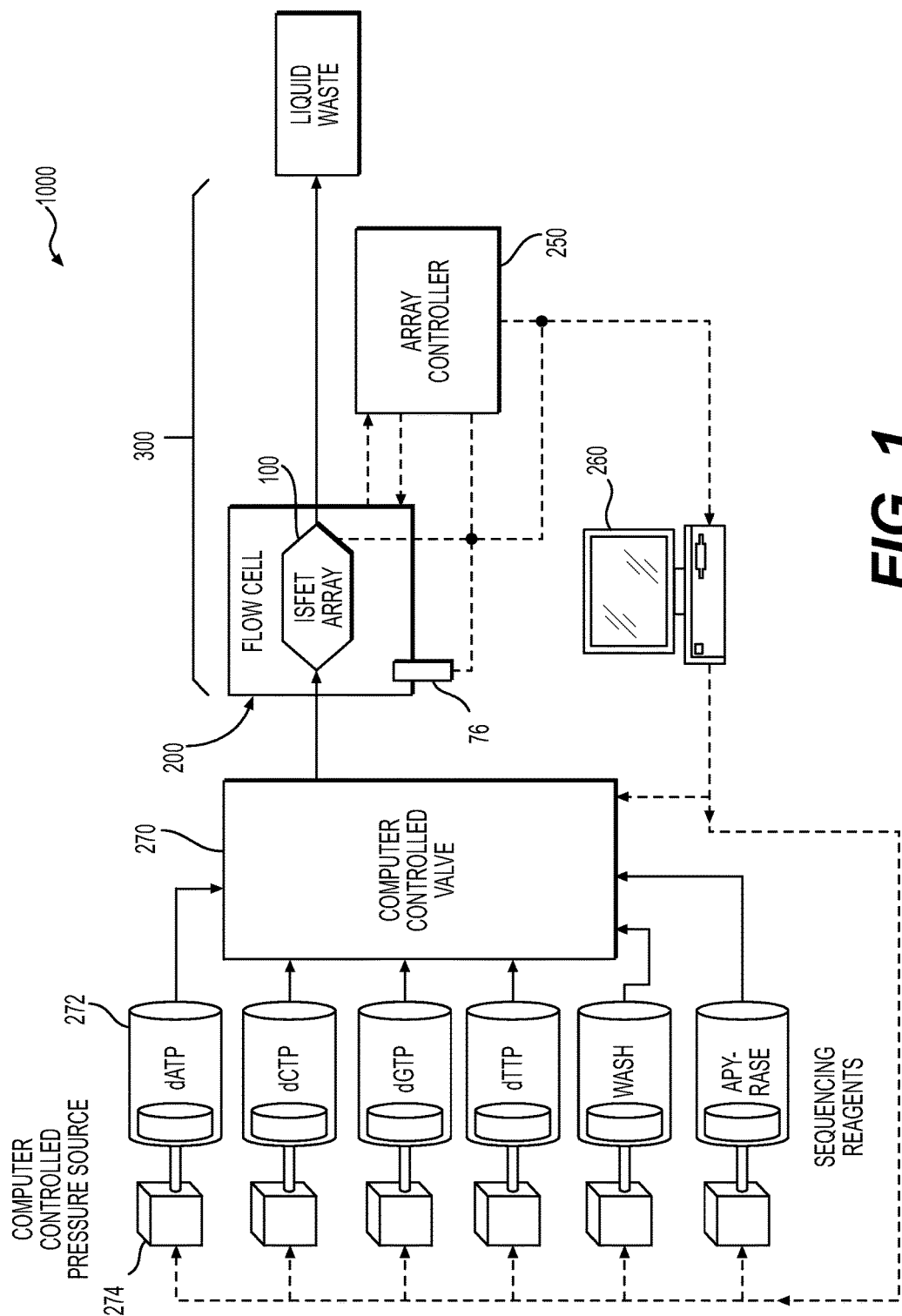
FIG. 1 depicts a nucleic acid processing system including a large scale chemFET array, according to exemplary embodiments of the present disclosure.

FIG. 1 depicts a nucleic acid processing system including a large scale chemFET array, according to exemplary embodiments of the present disclosure. An example of a nucleic acid processing system is a nucleic acid sequencing system. The chemFET sensors of the array are described for purposes of illustration as ISFETs configured for sensitivity to static and/or dynamic ion concentration, including but not limited to hydrogen ion concentration. However, it should be appreciated that the present disclosure is not limited in this respect, and that in any of the embodiments discussed herein in which ISFETs are employed as an illustrative example, other types of chemFETs may be similarly employed in alternative embodiments. Similarly, it should be appreciated that various aspects and embodiments of the present disclosure may employ ISFETs as sensors yet detect one or more ionic species that are not hydrogen ions.

The system 1000 may include a semiconductor/microfluidics hybrid structure 300 comprising an ISFET sensor array 100 and a microfluidics flow cell 200. The flow cell 200 may comprise a number of wells (not shown) disposed above corresponding sensors of the ISFET array 100. The flow cell 200 may be configured to facilitate the sequencing of one or more identical template nucleic acids disposed in the flow cell via the controlled and ordered introduction to the flow cell of a number of sequencing reagents 272 (e.g., dATP, dCTP, dGTP, dTTP (generically referred to herein as dNTP), divalent cations such as but not limited to Mg2+, wash solutions, and the like.

As illustrated in FIG. 1, the introduction of the sequencing reagents to the flow cell 200 may be accomplished via one or more valves 270 and one or more pumps 274 that are controlled by a computer 260. A number of techniques may be used to admit (i.e., introduce) the various processing materials (e.g., solutions, samples, reaction reagents, wash solutions, and the like) into the wells of such a flow cell. As illustrated in FIG. 1, reagents including dNTP may be admitted to the flow cell (e.g., via the computer controlled valve 270 and pumps 274) from which they diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100, or nucleic acids may be immobilized on the surfaces of sensors of the ISFET array 100.

The flow cell 200 in the system of FIG. 1 may be configured in a variety of manners to provide one or more analytes (or one or more reaction solutions) in proximity to the ISFET array 100. For example, a template nucleic acid may be directly attached or applied in suitable proximity to one or more pixels of the sensor array 100, or in or on a support material (e.g., one or more "beads") located above the sensor array but within the reaction chambers, or on the sensor surface itself. Processing reagents (e.g., enzymes such as polymerases) may also be placed on the sensors directly, or on one or more solid supports (e.g., they may be bound to the capture beads or to other beads) in proximity to the sensors, or they may be in solution and free-flowing. It is to be understood that the device may be used without wells or beads.

In the system 1000 of FIG. 1, according to one embodiment the ISFET sensor array 100 monitors ionic species, and in particular, changes in the levels/amounts and/or concentration of ionic species, including hydrogen ions. The species may be a result from a nucleic acid synthesis or sequencing reaction.

Various embodiments of the present disclosure may relate to monitoring/measurement techniques that involve the static and/or dynamic responses of an ISFET. It is to be understood that although the particular example of a nucleic acid synthesis or sequencing reaction is provided to illustrate the transient or dynamic response of chemFET, such as an ISFET, the transient or dynamic response of a chemFET, such as an ISFET, as discussed below may be exploited for monitoring/sensing other types of chemical and/or biological activity beyond the specific example of a nucleic acid synthesis or sequencing reaction.

Figure 2:
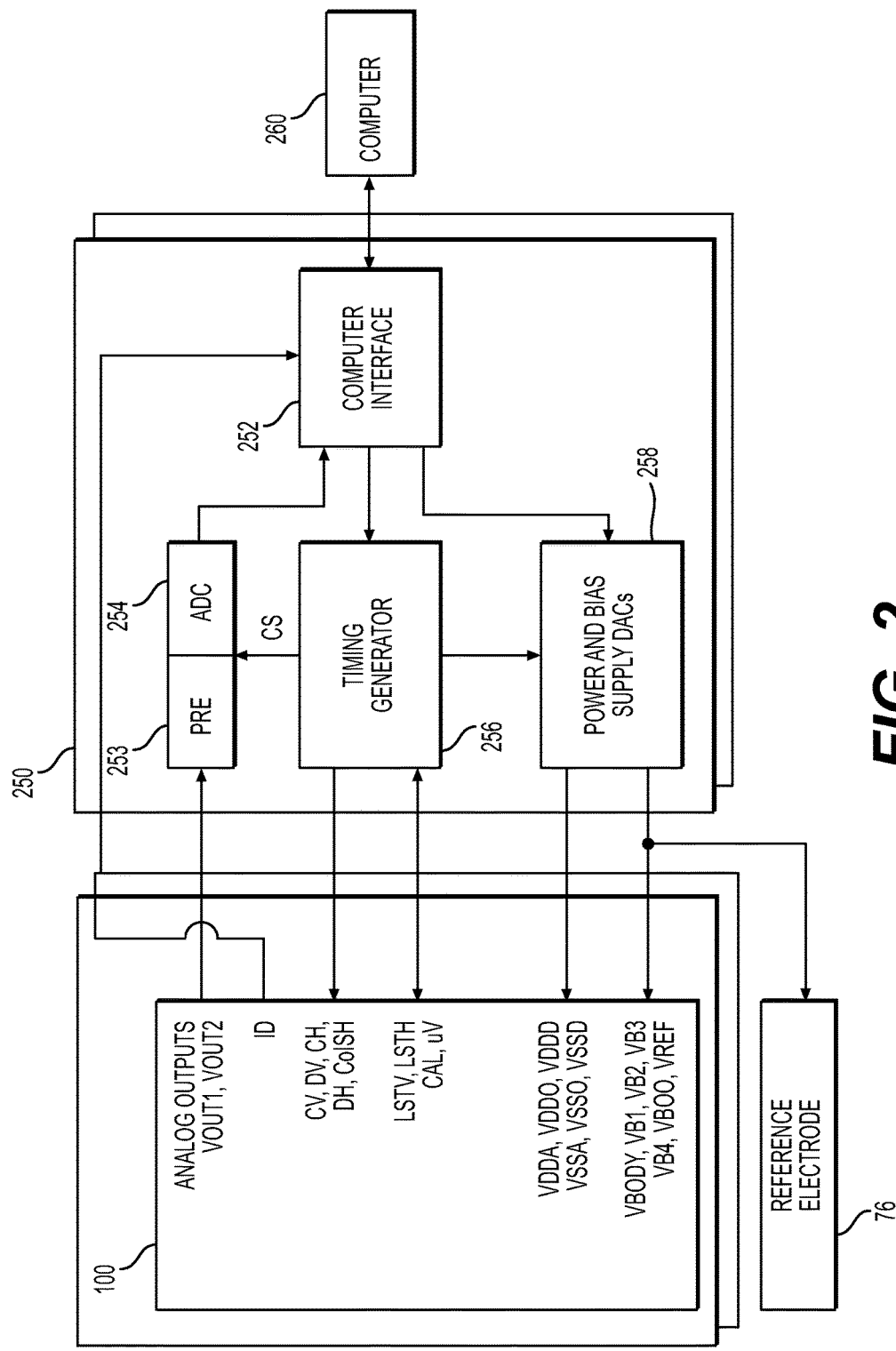
FIG. 2 depicts a block diagram of an exemplary CMOS IC chip implementation of a chemFET sensor array, according to exemplary embodiments of the present disclosure.

FIG. 2 depicts a block diagram of an exemplary CMOS IC chip implementation of a chemFET sensor array, according to exemplary embodiments of the present disclosure. As shown in FIG. 2, a sensor array 100 may be coupled to an array controller 250. The array controller 250 may be fabricated as a "stand alone" controller, and/or as one or more computer compatible "cards" forming part of a computer 260. The functions of the array controller 250 may be controlled by the computer 260 through an interface block 252 (e.g., serial interface, via USB port or PCI bus, Ethernet connection, etc.).

The array controller 250 may provide various supply voltages and bias voltages to the array 100, as well as various signals relating to row and column selection, sampling of pixel outputs and data acquisition. In particular, the array controller 250 may read one or more analog output signals (e.g., Vout1 and Vout2) including multiplexed respective pixel voltage signals from the array 100, and then may digitize these respective pixel signals to provide measurement data to the computer 260, which in turn may store and/or process the data. In some implementations, the array controller 250 also may be configured to perform or facilitate various array calibration and diagnostic functions.

As shown in FIG. 2, the array controller 250 may provide to the array 100 the analog supply voltage and ground (VDDA, VSSA), the digital supply voltage and ground (VDDD, VSSD), and the buffer output supply voltage and ground (VDDO, VSSO). In one exemplary embodiment, each of the supply voltages VDDA, VDDD and VDDO is approximately 3.3 Volts. In another implementation, the supply voltages VDDA, VDDD and VDDO may be as low as approximately 1.8 Volts. Each of these power supply voltages may be provided to the array 100 via separate conducting paths to facilitate noise isolation. In another aspect, these supply voltages may originate from respective power supplies/regulators, or one or more of these supply voltages may originate from a common source in a power supply 258 of the array controller 250. The power supply 258 also may provide the various bias voltages required for array operation (e.g., VB1, VB2, VB3, VB4, VBO0, VBODY) and the reference voltage VREF used for array diagnostics and calibration.

In another aspect, the power supply 258 includes one or more digital-to-analog converters (DACs) that may be controlled by the computer 260 to allow any or all of the bias voltages, reference voltage, and supply voltages to be changed under software control (i.e., programmable bias settings). For example, a power supply 258 responsive to computer control (e.g., via software execution) may facilitate adjustment of one or more of the supply voltages (e.g., switching between 3.3 Volts and 1.8 Volts depending on chip type as represented by an identification code), and/or adjustment of one or more of the bias voltages VB1 and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage VBODY for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions.

As also shown in FIG. 2, the reference electrode 76 which is typically employed in connection with an analyte solution to be measured by the array 100 (as discussed above in connection with FIG. 1), may be coupled to the power supply 258 to provide a reference potential for the pixel output voltages. For example, in one implementation the reference electrode 76 may be coupled to a supply ground (e.g., the analog ground VSSA) to provide a reference for the pixel output voltages. In other exemplary implementations, the reference electrode voltage may be set by placing a solution/sample of interest having a known pH level in proximity to the sensor array 100 and adjusting the reference electrode voltage until the array output signals Vout1 and Vout2 provide pixel voltages at a desired reference level, from which subsequent changes in pixel voltages reflect local changes in pH with respect to the known reference pH level. In general, it should be appreciated that a voltage associated with the reference electrode 76 need not necessarily be identical to the reference voltage VREF discussed above (which may be employed for a variety of array diagnostic and calibration functions), although in some implementations the reference voltage VREF provided by the power supply 258 may be used to set the voltage of the reference electrode 76.

Regarding data acquisition from the array 100, in one embodiment the array controller 250 of FIG. 2 may include one or more preamplifiers 253 to further buffer the one or more output signals (e.g., Vout1 and Vout2) from the sensor array 100 and provide selectable gain. In one aspect, the array controller 250 may include one preamplifier for each output signal (e.g., two preamplifiers for two analog output signals). In other aspects, the preamplifiers may be configured to accept input voltages from 0.0 to 1.8 Volts or 0.0 to 3.3 Volts, may have programmable/computer selectable gains (e.g., 1, 2, 5, 10 and 20) and low noise outputs (e.g., <10 nV/sqrtHz), and may provide low pass filtering (e.g., bandwidths of 5 MHz and 25 MHz). With respect to noise reduction and increasing signal-to-noise ratio, in one implementation in which the array 100 is configured as an application specific integrated circuit placed in a chip socket of a printed circuit board containing all or a portion of the array controller 250, filtering capacitors may be employed in proximity to the chip socket (e.g., the underside of a ZIF socket) to facilitate noise reduction. In yet another aspect, the preamplifiers 253 may have a programmable/computer selectable offset for input and/or output voltage signals to set a nominal level for either to a desired range.

The array controller 250 of FIG. 2 also comprises one or more analog-to-digital converters 254 (ADCs) to convert the sensor array output signals Vout1 and Vout2 to digital outputs (e.g., 10-bit or 12-bit) so as to provide data to the computer 260. In one aspect, one ADC 254 may be employed for each analog output of the sensor array 100, and each ADC 254 may be coupled to the output of a corresponding preamplifier 253 (if preamplifiers are employed in a given implementation). In another aspect, the ADC(s) 254 may have a computer-selectable input range (e.g., 50 mV, 200 mV, 500 mV, 1 V) to facilitate compatibility with different ranges of array output signals and/or preamplifier parameters. In yet other aspects, the bandwidth of the ADC(s) 254 may be greater than 60 MHz, and the data acquisition/conversion rate greater than 25 MHz (e.g., as high as 100 MHz or greater).

In the embodiment of FIG. 2, ADC acquisition timing and array row and column selection may be controlled by a timing generator 256. In particular, the timing generator 256 provides the digital vertical data and clock signals (DV, CV) to control row selection, the digital horizontal data and clock signals (DH, CH) to control column selection, and the column sample and hold signal COL SH to sample respective pixel voltages for an enabled row. The timing generator 256 also provides a sampling clock signal CS to the ADC(s) 254 so as to appropriately sample and digitize consecutive pixel values in the data stream of a given array analog output signal (e.g., Vout1 and Vout2). In some implementations, the timing generator 256 may be implemented by a microprocessor executing code and configured as a multi-channel digital pattern generator to provide appropriately timed control signals. In one exemplary implementation, the timing generator 256 may be implemented as a field-programmable gate array ("FPGA").

Various array control signals, as provided by the timing generator 256, may be used to acquire pixel data from the sensor array 100. For purposes of the following discussion, a "frame" may be a data set that includes a value (e.g., pixel output signal or voltage VS) for each pixel in the array, and a "frame rate" may be the rate at which successive frames may be acquired from the array. Thus, the frame rate corresponds essentially to a "pixel sampling rate" for each pixel of the array, as data from any given pixel is obtained at the frame rate.

A frame rate may be 20 frames/sec. However, it should be appreciated that arrays and array controllers according to the present disclosure are not limited in this respect, as different frame rates, including lower frame rates (e.g., 1 to 10 frames/second) or higher frame rates (e.g., 25, 30, 40, 50, 60, 70 to 100 frames/sec., etc.), with arrays having the same or higher numbers of pixels, are possible. In some exemplary applications, a data set may be acquired that includes many frames over several seconds to conduct an experiment on a given analyte or analytes. Several such experiments may be performed in succession, in some cases with pauses in between to allow for data transfer/processing and/or washing of the sensor array and reagent preparation for a subsequent experiment.

For example, with respect to a method for detecting nucleotide incorporation, appropriate frame rates may be chosen to sufficiently sample the ISFET's output signal. In some exemplary implementations, a hydrogen ion signal may have a full-width at half-maximum (FWHM) on the order of approximately 1 second to approximately 2.5 seconds, depending on the number of nucleotide incorporation events. Given these exemplary values, a frame rate (or pixel sampling rate) of 20 Hz may be sufficient to reliably resolve the signals in a given pixel's output signal. Again, the frame rates given in this example are provided primarily for purposes of illustration, and different frame rates may be involved in other implementations.

In regard to FIG. 2, and as discussed above, the array controller 250 reads one or more analog output signals (e.g., Vout1 and Vout2) including multiplexed respective pixel voltage signals from the array 100 and then digitizes these respective pixel signals to provide measurement data to the computer 260. In turn, the computer 260 may store and/or process the measurement data.

In an embodiment, the ADC(s) 254 may be controlled by the timing generator 256 via the sampling clock signal CS to sample the output signals Vout1 and Vout2 at a high data rate to provide two or more digitized samples for each pixel measurement, which may then be averaged. In an embodiment, two or more pixel measurements in successive frames may be averaged for each pixel of every frame considered. Here, the output is the average measurement for each pixel of all frames considered. As a result of this frame averaging technique, reduction in noise for each pixel may be achieved.

In regard to FIG. 2, the above-described frame averaging technique may occur in the array controller 250, the computer 260, or both the array controller 250 and the computer 260, according to an embodiment of the present disclosure. The computer 260 may store the pixel measurement data for further processing, according to an embodiment of the present disclosure. In another embodiment, the pixel measurement data may be stored in a memory storage device (not shown) that is external to the array controller 250 and the computer 260.

Variable frame rate averaging may also be performed on the data sampled from the sensor array (e.g., array 100 of FIG. 2). Variable frame rate averaging is similar to the frame averaging technique discussed above with the addition of allowing a variable number of frames to be averaged together. A benefit, among others, of variable frame rate averaging is that the number of frames averaged and outputted as a single frame may be done at any point during the data acquisition process. Once the variable frame rate averaging is performed on the data sampled from the sensor array, a key frame delta compression may be performed on the resulting data to further compress the data to be stored.

With faster sampling data rates and higher densities of sensor arrays, the pixel measurement data may consume a large amount of memory on the computer 260 and/or an external memory storage device. It is thus desirable to reduce memory consumption while maintaining the quality of the pixel measurement data. A goal of at least certain exemplary methods discussed in detail below, among others, is to accurately capture data associated with a biological/chemical event, while reducing noise associated with the data. This goal may be achieved by implementing compression techniques described below. As a result, the amount of data stored (e.g., in the computer 260 of FIG. 2 or an external memory storage device) may be reduced.

In one embodiment of the present disclosure, a compression technique may include processing and storing sequencing data in a frequency domain. In particular, a frequency domain compression technique may compress a small block of spatially correlated wells. For example, the frequency domain compression technique may compress data from a sub-array ("block") of a sensory array of about 50×50 wells.

A truncated mean spectrum may be stored as a key frame, and an entropy of each frequency component may be estimated based on the key frame. A number of bits may be allocated for each frequency component to represent an individual well's differences from the key frame. In-phase and quadrature scaling values for each frequency component may be calculated, and well differences may be scaled. Then, the reduced bit-range values may be compressed.

In one embodiment of the present disclosure, all frequency components are not required for adequate signal reconstruction. For example, the first 15% to 30% of a frequency component spectrum may be used to generate the key frame, and the first 15% to 30% of an individual well's frequency component spectrum may be used to estimate differences from the key frame.

In various embodiments, individual frequency components may include less unique information (e.g., have lower entropy) than other frequency components. Therefore, individual frequency components may require fewer bits to represent their differences from the key frame. In another embodiment, a DC term of a frequency spectrum may be discarded to remove an offset. In yet another embodiment of the present disclosure, negative frequency values of a frequency domain spectrum may be discarded, as a source signal represents real components. A negative frequency value may be viewed as a complex conjugate of the positive frequency components. A benefit of at least certain embodiments of the present disclosure is that the compression techniques discussed herein do not require information from a period of time before measurement or from a period of time prior to mid measurement.

Figure 3:
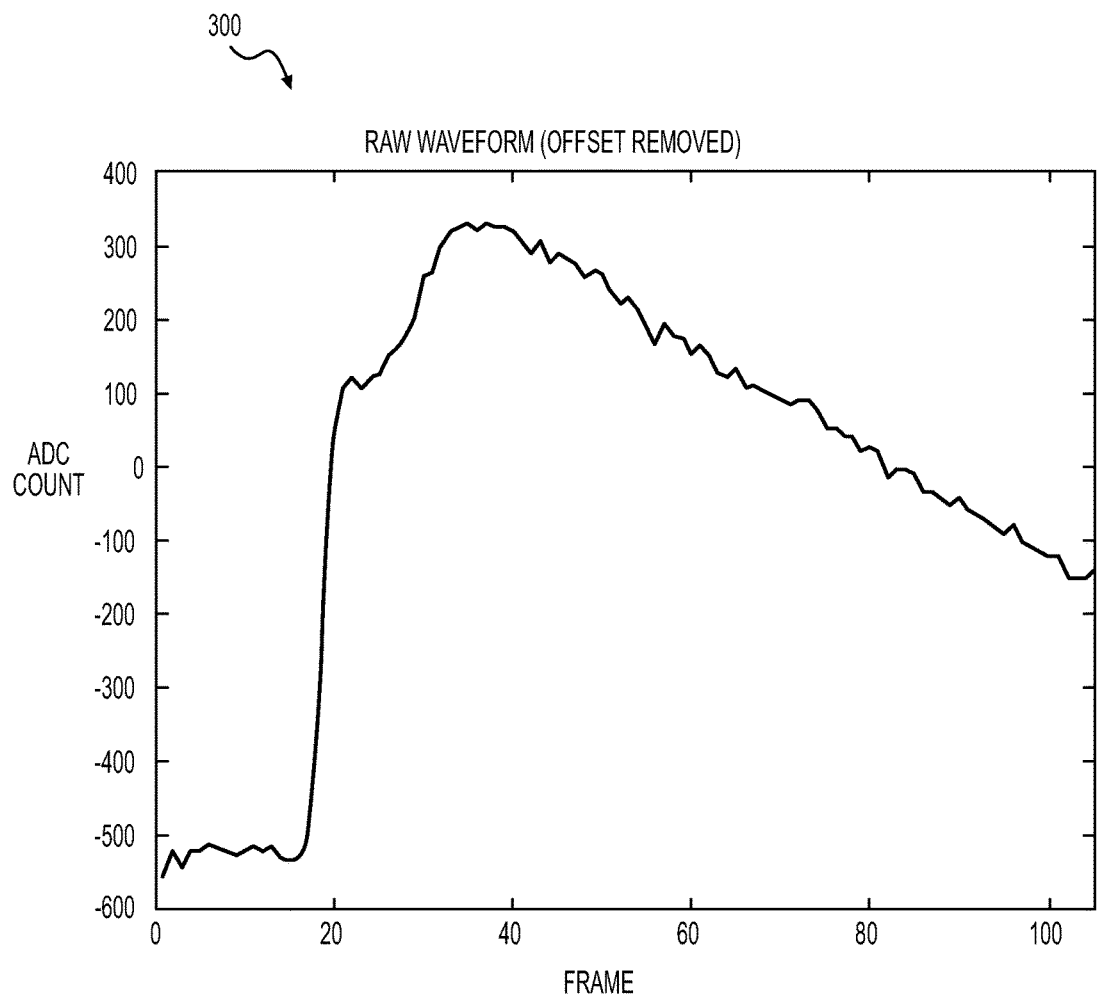
FIG. 3 depicts a time-domain waveform, according to exemplary embodiments of the present disclosure.

In an embodiment, the time-domain waveform data of every well may be converted into its frequency-domain representation using an integral transform, such as a Fourier transform. FIG. 3 depicts a time-domain waveform, according to exemplary embodiments of the present disclosure. The raw waveform, as shown in FIG. 3, may have an offset removed. The waveform 300 depicts a stepwise change in the concentration of one or more ionic species in an analyte solution in fluid contact with an ISFET array (e.g., array 100 of FIG. 1). The waveform 300 may represent a dynamic response of an ISFET array to a change in ionic strength of the analyte solution in fluid contact with the ISFET array. The x-axis of the waveform 300 represents a frame number, which may be a function of time. Depending on a clock signal provided by a timing generator (e.g., timing generator 256 of FIG. 2), the data rate at which frames are sampled from the ISFET array may vary, as would be understood by a person of ordinary skill in the art. The y-axis of the waveform 300 represents a number of counts, which is representative of voltage measured by the ISFET array.

The waveform 300 of FIG. 3 may include an ISFET array response "pulse," which is an ISFET array characteristic also known as an "ion-step" or "stepwise" response. The waveform, as shown in FIG. 3, may be converted into its frequency-domain representation by using an integral transform. The transform used to convert the time-domain waveform data to frequency-domain waveform spectrum data may include one or more of a Fourier transform, a Fourier sine transform, a cosine transform, a discrete cosine transform, a Fourier cosine transform, a Hartley transform, a Mellin transform, a two-sided Laplace transform, a Laplace transform, a Weierstrass transform, a Hankel transform, an Abel transform, a Hilbert transform, a Poisson kernel, and/or an identity transform. The following documents relate to integral transforms and are incorporated by reference herein in their entirety: Narasimha, M, et al., *On the Computation of the Discrete Cosine Transform*, IEEE Transactions on Communications, vol. COM-26, no. 6, pp. 934-936 (1978); and Martucci, S., *Symmetric Convolution and the Discrete Sine and Cosine Transforms*, IEEE Transactions on Signal Processing, vol. 42, no. 5, pp. 1038-1051 (1994).

Figure 4:
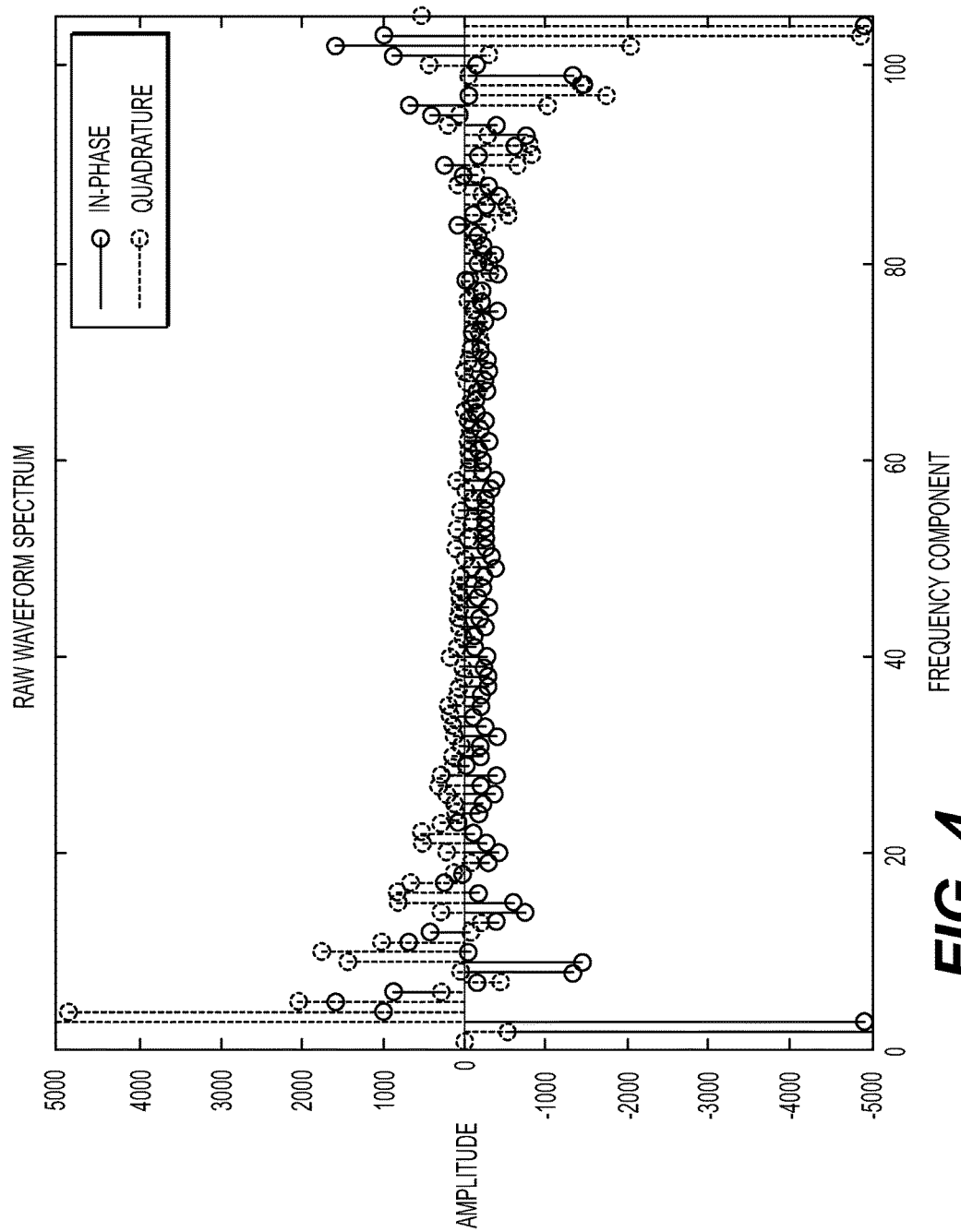
FIG. 4 depicts a frequency-domain waveform spectrum, according to exemplary embodiments of the present disclosure.

FIG. 4 depicts a frequency-domain waveform spectrum, according to exemplary embodiments of the present disclosure. The raw waveform spectrum, as shown in FIG. 4, may be obtained by converting the time-domain waveform data of FIG. 3 using a Fourier transform. As shown in FIG. 4, the solid lines depicts in-phase data and the dashed lines depicts quadrature data. As may be apparent from the exemplary frequency-domain waveform spectrum of FIG. 4, the right half of the spectrum may be a complex conjugate of the left half of the spectrum (i.e., the quadrature component may be inverted).

Figure 5:
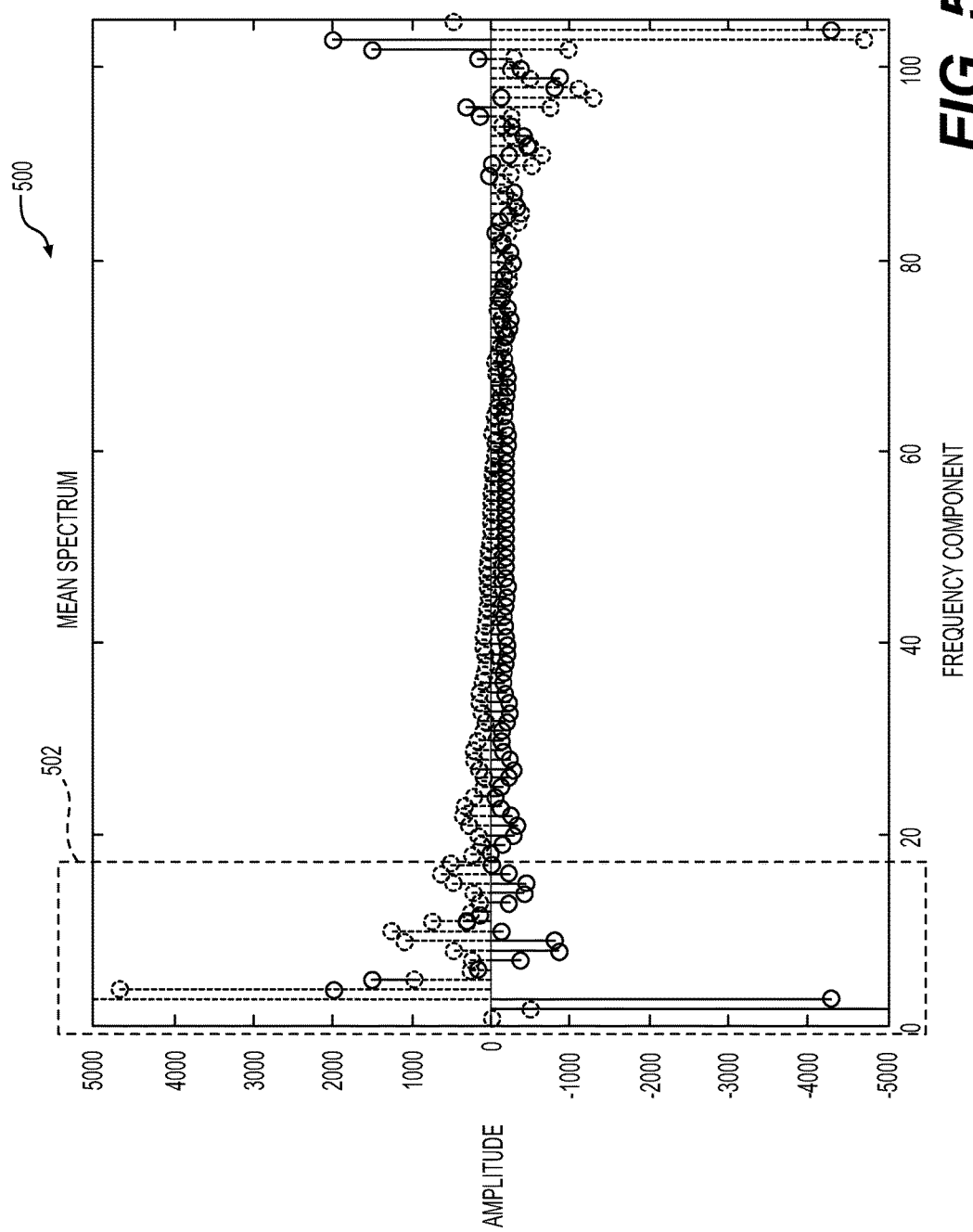
FIG. 5 depicts an average "mean" spectrum of all of the wells in a sensor array, according to exemplary embodiments of the present disclosure.

Upon obtaining the frequency-domain waveform spectrum for each well of a sensor array, an average ("mean") spectrum of all of the wells of the array may be generated. FIG. 5 depicts an average "mean" spectrum of all of the wells in a sensor array, according to exemplary embodiments of the present disclosure. In one embodiment of the present disclosure, all of the frequency components of the mean spectrum may be preserved. In another embodiment of the present disclosure, a portion of the frequency components may be preserved. For example, as shown in FIG. 5, the boxed portion 502 of frequency components may be preserved. In this example, the first 16 frequency components may be used, and the other frequency components (i.e., 17 and up) may be discarded. In the example embodiment, the non-DC frequency components may be used, and a DC=0 Hz component may be a constant offset (FIG. 6).

Figure 6:
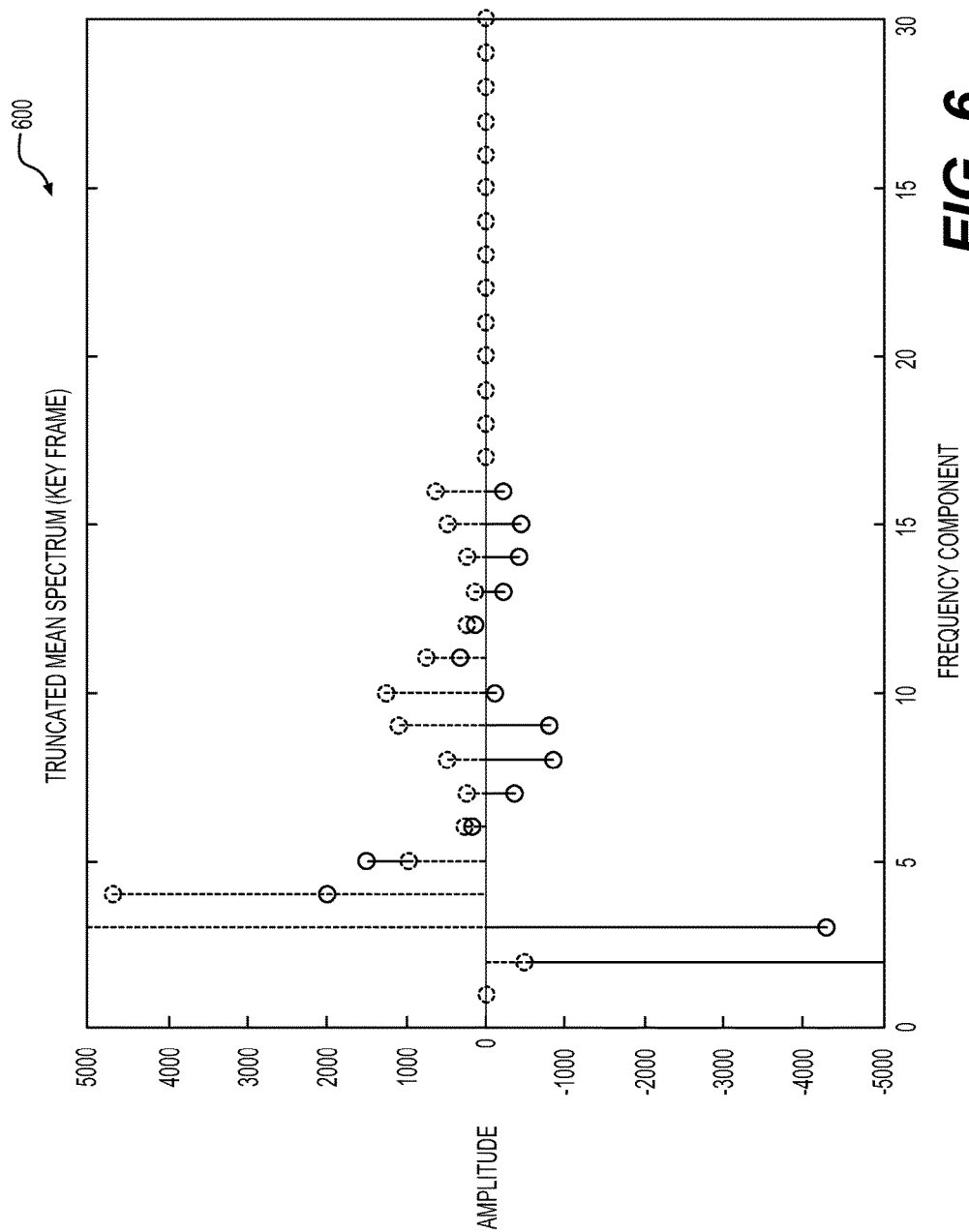
FIG. 6 depicts a truncated average "mean" spectrum of the average "mean" spectrum shown in FIG. 5, according to exemplary embodiments of the present disclosure.

FIG. 6 depicts a truncated average "mean" spectrum of the average "mean" spectrum shown in FIG. 5, according to exemplary embodiments of the present disclosure. The truncated average "mean" spectrum may be the first 15% to 30% of an average frequency spectrum. The truncated mean spectrum may be stored as a key frame for the compression technique.

Figure 7:
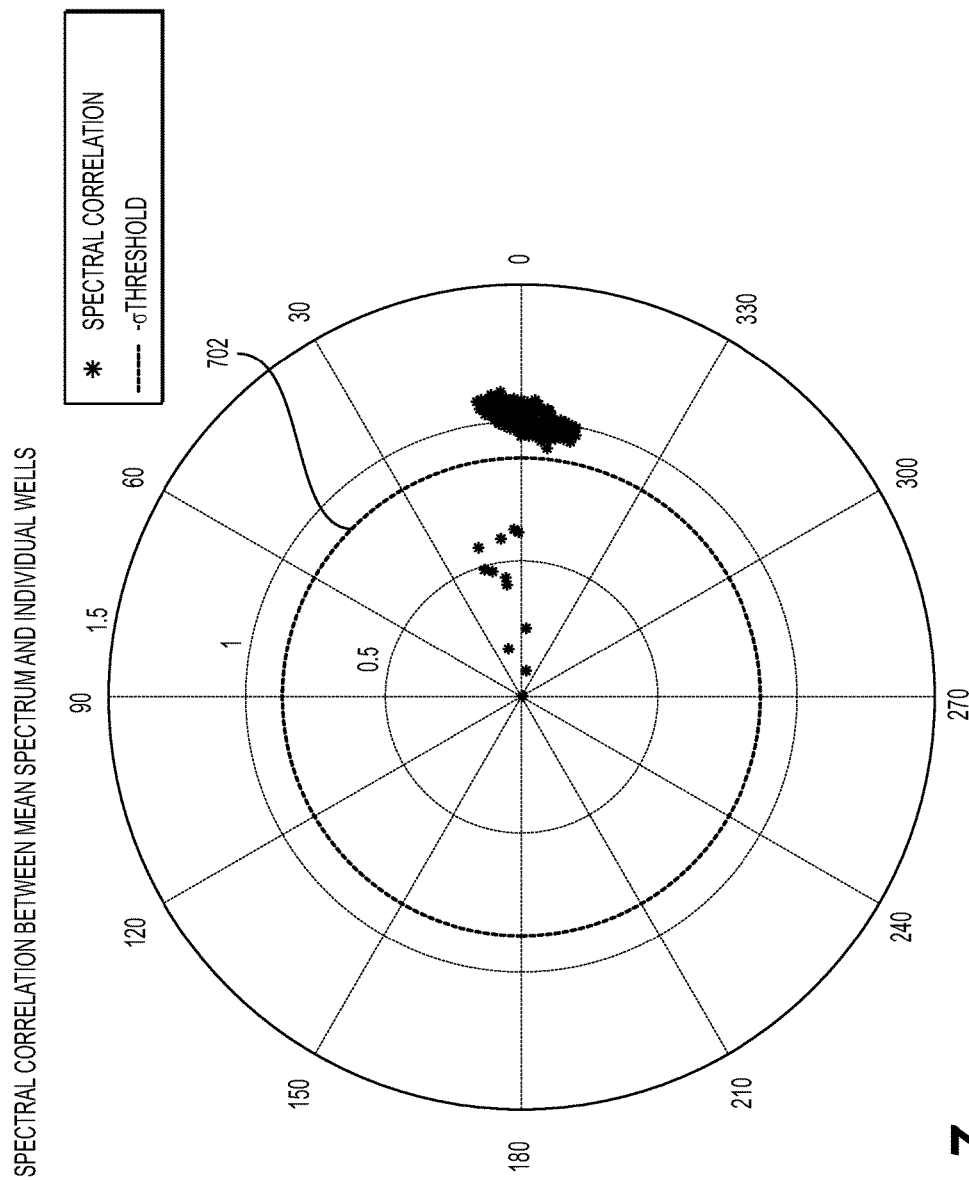
FIG. 7 depicts a spectral correlation between the average "mean" spectrum (key frame) and individual wells, according to exemplary embodiments of the present disclosure.

Once the key frame has been generated, an entropy of each frequency component of an individual well may be estimated based on the key frame. FIG. 7 depicts a spectral correlation between the average "mean" spectrum (key frame) and individual wells, according to exemplary embodiments of the present disclosure. Wells that may be producing poor and/or bad data then may be identified.

In one embodiment of the present disclosure, bad data from wells may be identified by calculating a correlation coefficient ("C") for each well vector ("W") with a complex conjugate key frame vector ("K"), which may be represented by the formula: C=K'*W. As shown in FIG. 7, individual wells that provide good data may form a tight clustering. Wells with "C" values more than one standard deviation below the mean may be considered wells that produce bad data. For example, wells that are inside of the dashed circle 702 of FIG. 7 may be more than one standard deviation below the mean and may be discarded.

Figure 8:
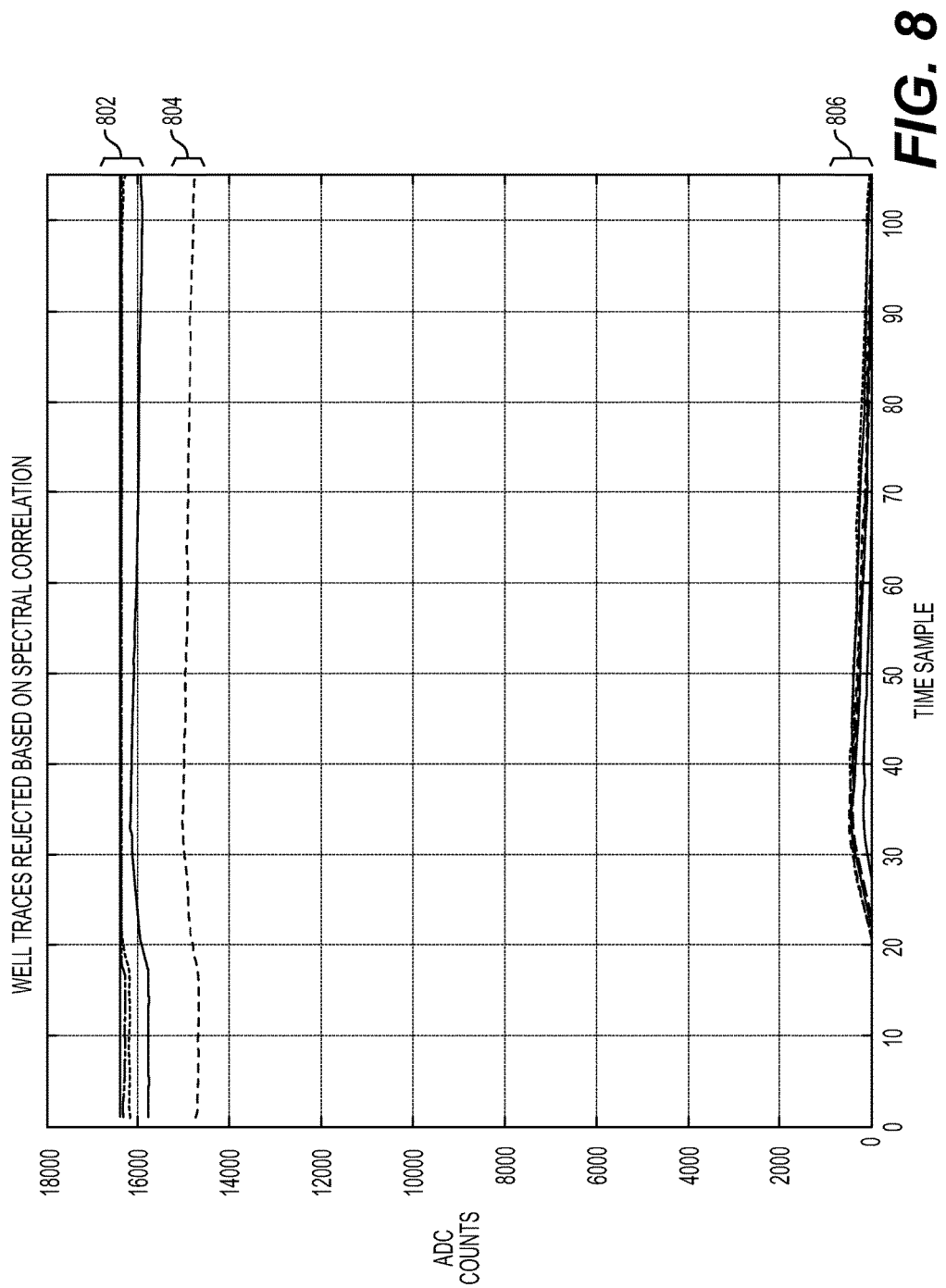
FIG. 8 depicts well traces rejected based on spectral correlation, according to exemplary embodiments of the present disclosure.

Wells with values more than one standard deviation below the mean may be removed as being pinned, clipped, and/or misbehaving data, as shown in FIG. 8. FIG. 8 depicts well traces rejected based on spectral correlation, according to exemplary embodiments of the present disclosure. As shown in FIG. 8, the top lines 802 indicate wells that have been pinned, the middle lines 804 indicate wells that are providing misbehaving data, and the bottom lines 806 indicate wells that have been clipped.

As mentioned above, for each well of a sensor array, frequency elements may be obtained. Then, for each well, each of the frequency elements may be multiplied by the complex conjugate of the corresponding key frame frequency element. The population magnitude mean, magnitude standard deviation, and phase angle standard deviation may then be calculated for each multiplied frequency element. Frequency elements having more information content (higher entropy) may have a larger phase and relative magnitude standard deviation.

Figure 9A:
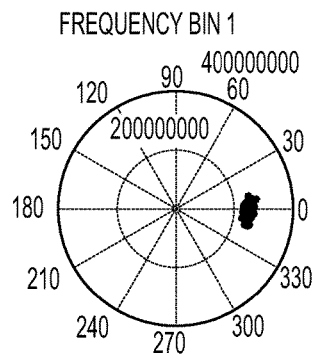
FIGS. 9A-9I depict various exemplary spectral correlations between the average "mean" spectrum and individual wells, according to exemplary embodiments of the present disclosure.
Figure 9B:
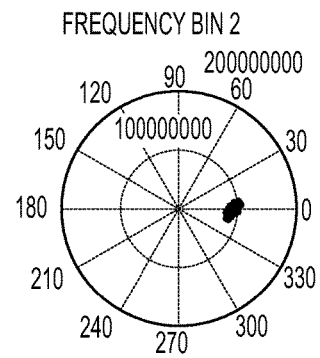
Figure 9C:
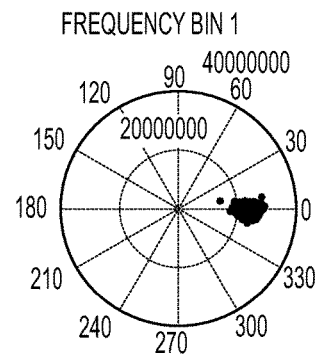
Figure 9D:
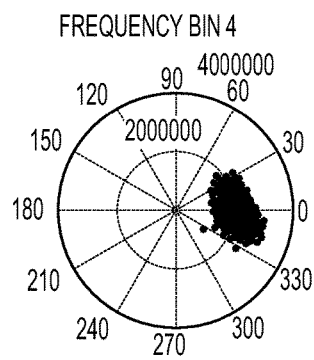
Figure 9E:
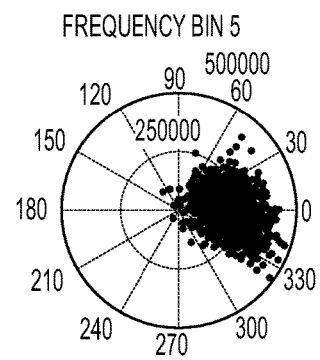
Figure 9F:
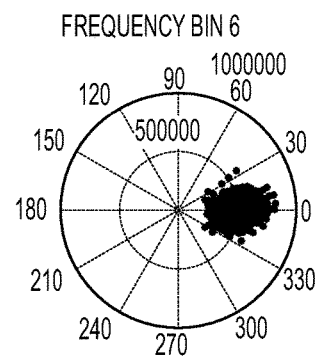
Figure 9G:
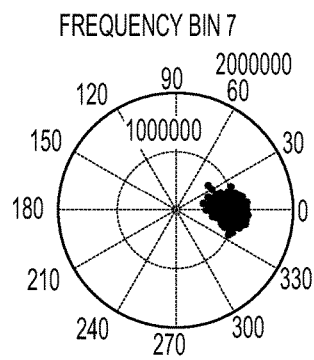
Figure 9H:
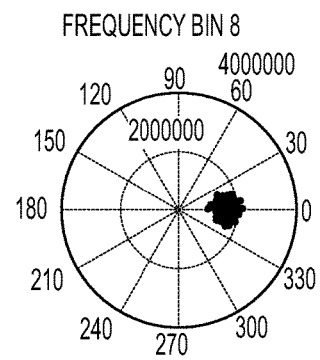
Figure 9I:
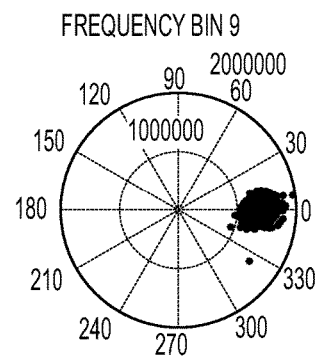

FIGS. 9A-9I depict various exemplary spectral element correlations between the average "mean" spectrum and individual wells, according to exemplary embodiments of the present disclosure. As shown in FIGS. 9A-9C depict exemplary spectral element correlations between the average "mean" spectrum and individual wells having very high entropy. FIGS. 9D, 9F, and 9H depict exemplary spectral correlations between the average "mean" spectrum and individual spectral elements having high entropy. FIGS. 9G and 9I depict exemplary spectral correlations between the average "mean" spectrum and individual spectral elements having medium entropy. FIG. 9E depicts exemplary spectral correlations between the average "mean" spectrum and individual spectral elements having medium to low entropy.

Upon calculating the population magnitude mean, magnitude standard deviation, and phase angle standard deviation for each frequency element, the number of bits required to encode the frequency components of a well may be calculated. The number of bits required to encode each frequency element delta value (minimum required bits [minBits] to maximum required bits [maxBits]) may be calculated based on an entropy value for each frequency element. The entropy value for each frequency element n ("$\varepsilon_n$") may be equal to the phase angle standard deviation of the frequency element n ("std(angle$_n$)") multiplied by the magnitude standard deviation of the frequency element n ("std(mag$_n$)"), as depicted by the formula: $\varepsilon_n$=std(angle$_n$)× std(mag$_n$).

Upon calculating the entropy value for each frequency element, the entropy values may be normalized (i.e., scaled to have a maximum value of 1). Then, the normalized entropy values may be converted to bits. The bits required for each frequency element n ("bits$_n$") may be equal to (the maximum bits required minus 1 ("(maxBits−1)")) plus the log 2 of the normalized entropy value of the frequency element n ("$\log_2$ $\varepsilon$_norm$_n$"), as depicted by the formula: bits$_n$=(maxBits−1)+$\log_2$ $\varepsilon$_norm$_n$. The minimum value of bits$_n$ may be limited to (minBits−1). Additionally, the bits required for each frequency element n may be increased by one (1) to account for a signing of bit values.

Figure 10:
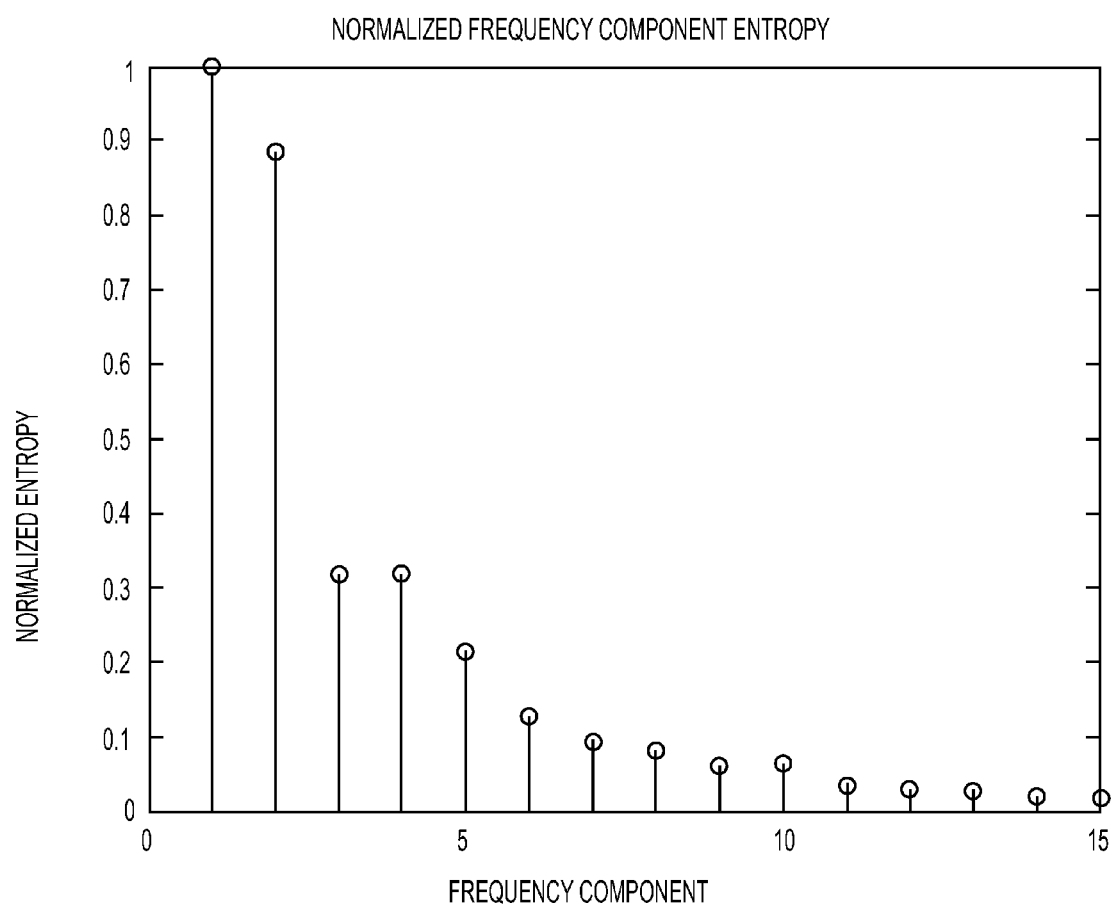
FIG. 10 depicts a normalized frequency component entropy, according to exemplary embodiments of the present disclosure.
Figure 11:
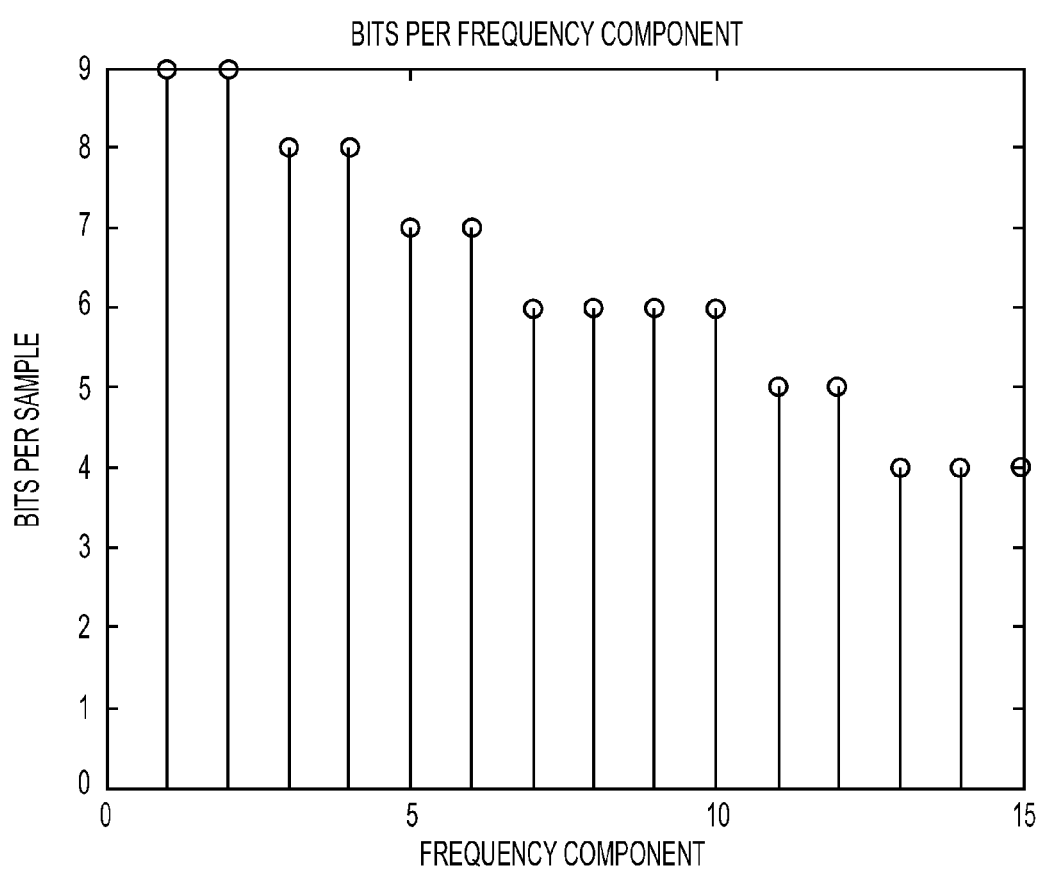
FIG. 11 depicts bits per frequency component, according to exemplary embodiments of the present disclosure.

FIG. 10 depicts a normalized frequency component entropy, according to exemplary embodiments of the present disclosure. FIG. 11 depicts bits per frequency component, according to exemplary embodiments of the present disclosure. In an example embodiment, minBits may equal three (3) and maxBits may equal nine (9). The data of this example may be encoded as signed integers, which is why the magnitude is calculated and limited using (minBits−1) and (maxBits−1), with the sign bit added at the end. Of course, a person of ordinary skill in the art will understand that minBits and maxBits may be assigned other values.

Figure 12A:
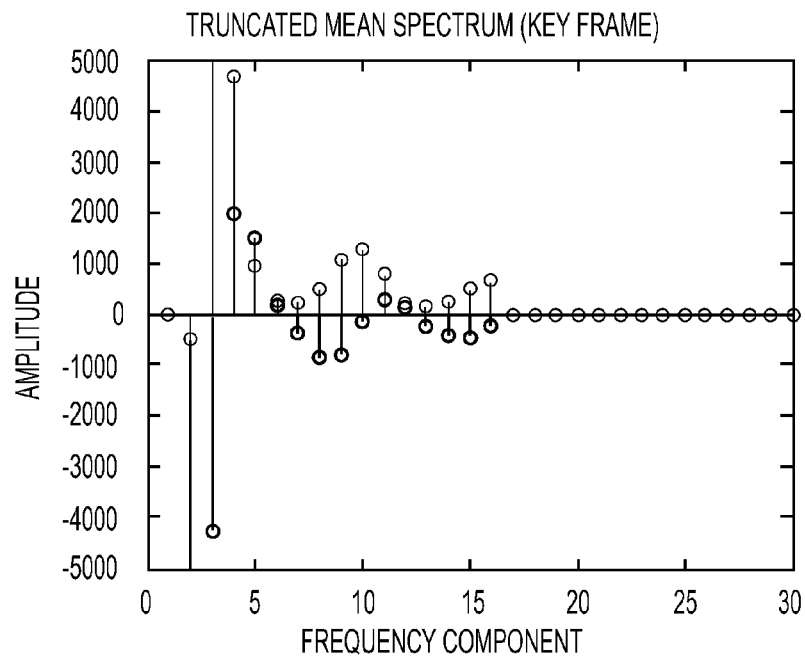
FIGS. 12A and 12B depict an exemplary key frame and a well's spectrum, respectively, according to exemplary embodiments of the present disclosure.
Figure 12B:
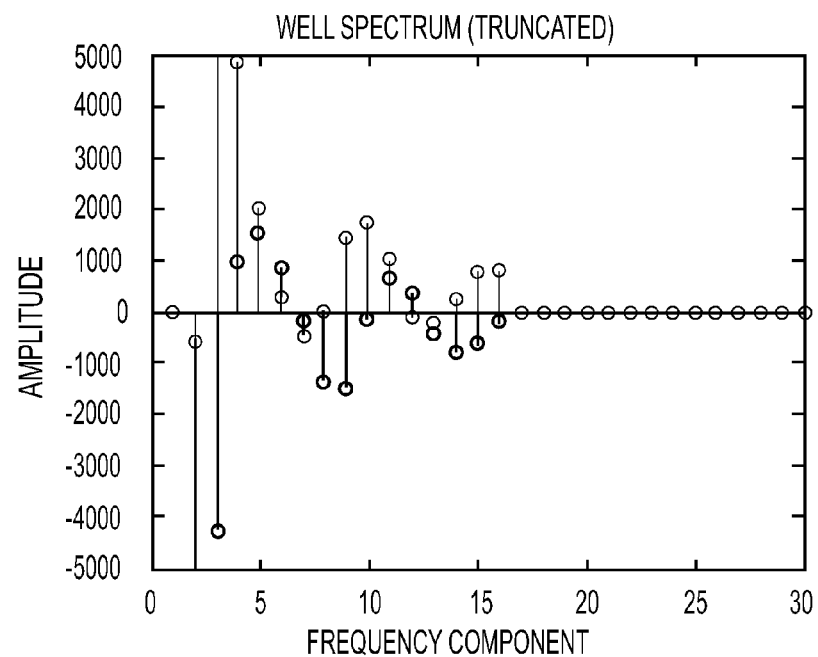
Figure 13:
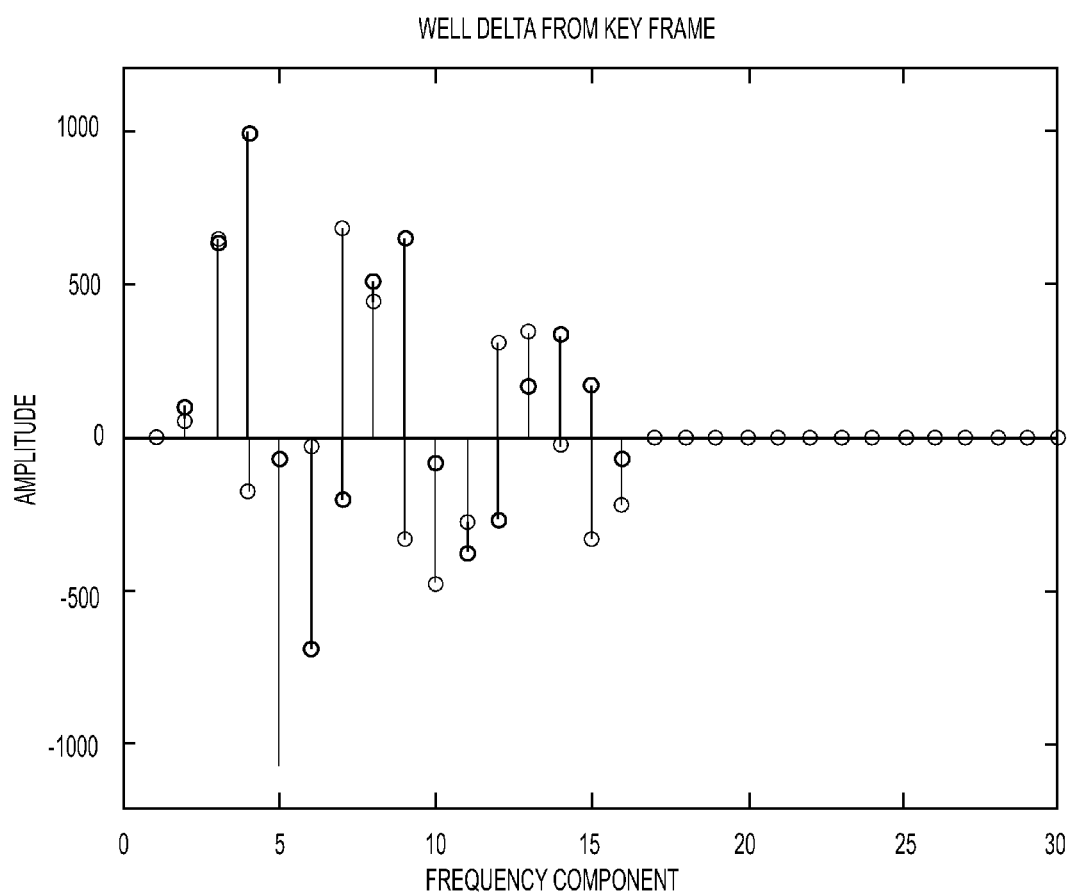
FIG. 13 depicts an exemplary well spectrum delta from a key frame, according to exemplary embodiments of the present disclosure.

With the key frame calculated, a difference between each well's truncated spectrum and the key frame spectrum may be calculated. FIGS. 12A and 12B depict an exemplary key frame and a well's truncated spectrum, respectively, according to exemplary embodiments of the present disclosure. FIG. 13 depicts an exemplary well spectrum delta from a key frame, according to exemplary embodiments of the present disclosure.

After well spectrum differences from a key frame are calculated, a scaling vector for the in-phase data ("scale$_{n_I}$") and a scaling vector for the quadrature data ("scale$_{n_Q}$") frequency component delta values may be calculated. A maximum magnitude of all the deltas for in-phase data of each frequency component ("max (abs(deltaVec$_{n_I}$))") may first be determined. Then, the scale of the in-phase data of each frequency component n may be calculated. The maximum magnitude of all the deltas for in-phase data of each frequency component ("max (abs(deltaVec$_{n_I}$))") may be divided by one less than two to the power of bits required for each frequency element n ("bits$_n$") minus one, which may be represented by the formula: scale$_{n_I}$=max (abs(deltaVec$_{n_I}$))÷(($2^{bits_n-1}$)−1).

A maximum magnitude of all the deltas for quadrature data of each frequency component ("max (abs(deltaVec$_{n_Q}$))") may first be determined. Then, the scale of the quadrature data of each frequency component n may be calculated. The maximum magnitude of all the deltas for quadrature data of each frequency component ("max (abs(deltaVec$_{n_Q}$))") may be divided by one less than two to the power of bits required for each frequency element n ("bits$_n$") minus one, which may be represented by the formula: scale$_{n_Q}$=max (abs(deltaVec$_{n_Q}$))÷(($2^{bits_n-1}$)−1).

In the above discussed example, the scale vectors of the in-phase data and quadrature data may be calculated using bits$_n$−1 because the values calculated may be an unsigned magnitude value. Additionally, the bits$_n$−1 may be used to ensure that a bit is reserved for a signed value.

After calculating the scaling vectors for the in-phase data and quadrature data frequency component delta values, the frequency delta values may be encoded. To encode the in-phase data of the frequency component ("encoded$_{n_I}$"), each frequency component in-phase data value ("deltaVec$_{n_I}$") may be divided by the scaling vector for the in-phase data ("scale$_{n_I}$"), and then may be rounded to the nearest integer, as shown in the formula: encoded$_{n_I}$=round (deltaVec$_{n_I}$÷scale$_{n_I}$). To encode the quadrature data of the frequency component ("encoded$_{n_Q}$"), each frequency component quadrature data value ("deltaVec$_{n_Q}$") may be divided by the scaling vector for the quadrature data ("scale$_{n_Q}$"), and then may be rounded to the nearest integer, as shown in the formula: $encoded_{n_Q}=round(deltaVec_{n_Q} \div scale_{n_Q})$.

The encoded frequency delta values may then be packed. The nominated number of encoded bits from each encoded value may be packed into regular data words for storage. Packing may be performed by using bit shifting and/or by using a logical OR. For example, packing may be represented by the following: Data2write=encodedI[0]| (encodedQ[0]<<bits$_n$[0])| encodedI[1]| (encodedQ[1]<<bits$_n$[1])| and so on.

The packed data may be stored with a header, and each sub-array of the sensor array may have a respective header and packed data. The header may include the number of frequency elements per well, the number of original time domain samples, the key frame data (for both the in-phase data and quadrature data), scaling vectors (for both the in-phase data and quadrature data), and bits-per-element vector. In one embodiment, the compressed well data may be packed and stored sequentially. The bits of a given well may be stored sequentially and wells may be stored in sequential raster (or any pre-defined) order. The number of bits required per compressed well may be double the sum of the "bits-per-element" vector.

Figure 14:
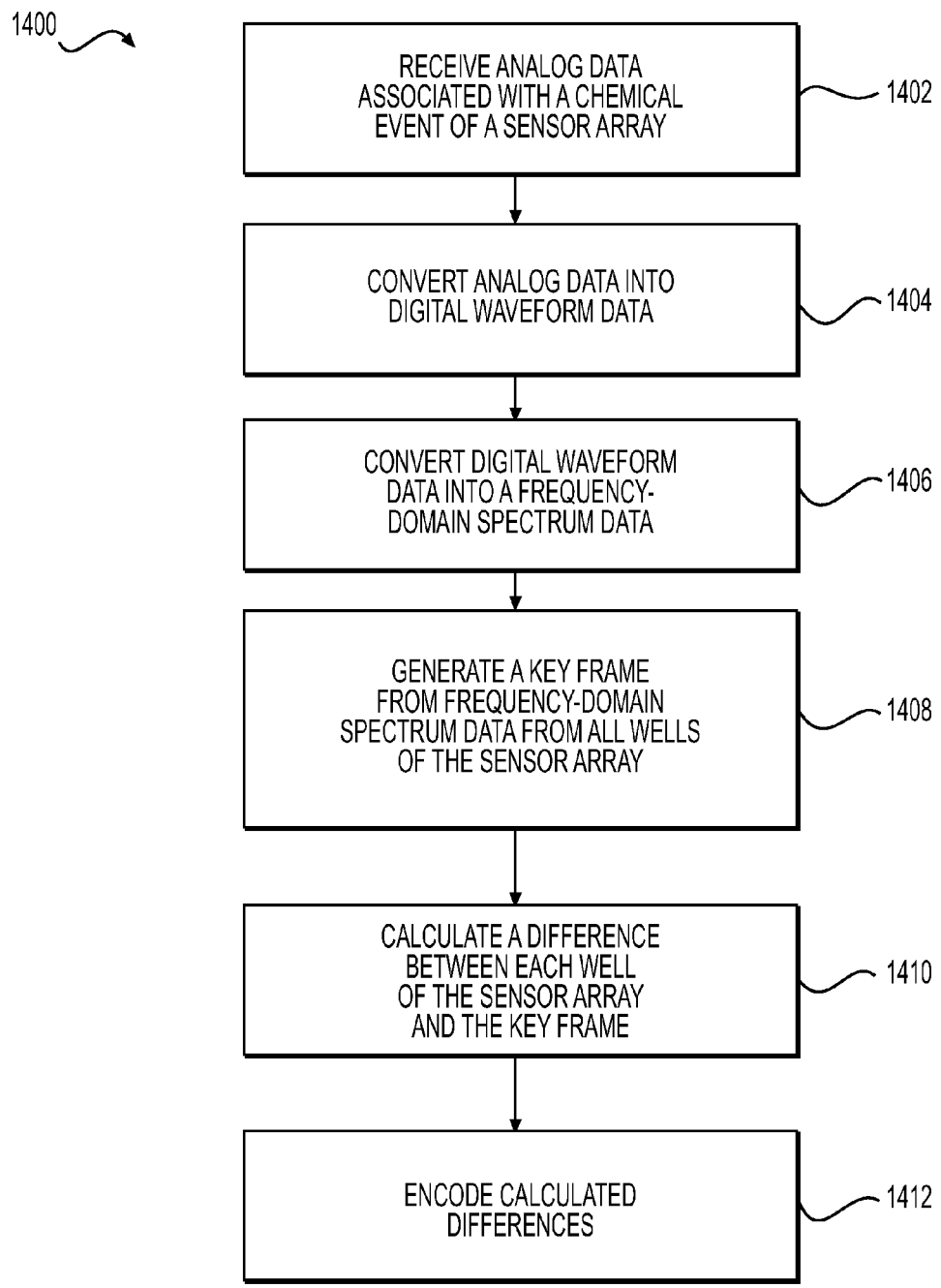
FIG. 14 depicts a compression method, according to exemplary embodiments of the present disclosure.

FIG. 14 depicts a compression method 1400, according to an exemplary embodiment of the present disclosure. In step 1402, an analog output or waveform associated with a chemical event occurring in each well or other reaction area of a sensor array may be received. In step 1404, the analog output or waveforms may be converted into a digitized output or waveforms comprising a plurality of frames using a digitizer.

The digitizer may be of any suitable digitizer type, and may convert the analog output or waveform to 14 bit data, for example. Various conversion frame rates may be used. For example, the rate may be 0.008478 second/frame (e.g., Ion 314™ Chip by Ion Torrent™), 0.034402 second/frame (e.g., Ion 316™ Chip by Ion Torrent™), 0.061075 second/frame (e.g., Ion 318™ Chip by Ion Torrent™), and 0.033 second/frame (e.g., Ion Proton™ chip I or Ion P1™ Chip by Ion Torrent™). More generally, the rate may be selected between about 0.004 second/frame and about 0.333 second/frame.

In an alternative embodiment, a digitized output or waveform data comprising a plurality of frames may be received. The waveform data may include a time-domain based waveform of each well have a plurality of frames.

In step 1406, the digitized, time-domain based, waveform of each well may be converted into a frequency-domain spectrum. The digitized, time-domain based, waveform of each well may be converted into the frequency-domain spectrum by using an integral transform, such as a Fourier transform. Then, at step 1408, a key frame may be generated from the frequency-domain spectrum data from all of the wells. In one embodiment, the key frame may be the average (mean) spectrum of all of the wells. Alternatively, a truncated average "mean" spectrum of the average "mean" spectrum may be used to generate the key frame. For example, the key frame may be generated from the first 15% to 30% of an average frequency spectrum.

In step 1410, for each well of a sensor array, a difference between the key frame and the well may be calculated. Upon calculating the differences between the key frame and each of the wells, at step 1412, the differences may be encoded, as discussed above.

An example of source code for compression of sequencing data is provided at the end of the detailed description.

After the well data has been encoded and stored, the key frame and delta information may be used to reconstruct the spectrum of each well. In order to accurately reconstruct the spectrum of each well, negative frequencies may be reconstructed from the complex conjugate of the positive frequency spectrum. Further, higher order frequency components (positive and negative) may be padded with zeros. After the frequency-domain spectrum has been reconstructed, an inverse of the integral transform may be used to convert the reconstructed spectrum back into a time-domain waveform. For example, an inverse Fourier transform may be used to convert the reconstructed spectrum back into the time-domain waveform. The reconstructed time-domain waveform may be pure real, zero-mean (no complex components).

An example of source code for decompression (expansion) of sequencing data is provided below:

```
% Differential Fourier Compression - Expander
function [data] = DFExpand(keyframe, bitsPerFreq, scale, deltas, timePts)
% Step 1 - construct spectrum template
freqPts = length(bitsPerFreq);
posLength = ceil(timePts / 2);
templateFreq = zeros(1, posLength);
templateFreq(2:(freqPts+1)) = keyframe;
% Step 2 - add delta values to template to reconstruct positive half of well
% spectrums
numWells = size(deltas,2);
scaleIdx = find(bitsPerFreq)+1; % get frequency bin index values of deltas
freqData = zeros(posLength, numWells); % pre-allocate
for idx = 1:numWells
    freqData(:,idx) = templateFreq;
    freqData(scaleIdx,idx) = freqData(scaleIdx,idx) + (real (scale.') .*
real(deltas(: idx))) + 1i*(imag(scale.') * imag(deltas(:,idx)));
end
% Step 3 - Synthesize negative frequency data from complex conjugate of
% positive spectrum data
freqData((posLength+1):timePts,:) = (freqData(posLength:-1:2,:)').';
data = zeros(size(freqData)) ; % pre-allocate
for idx = 1:numWells
    data(:,idx) = ifft(freqData(:,idx));
end
```

Figure 15:
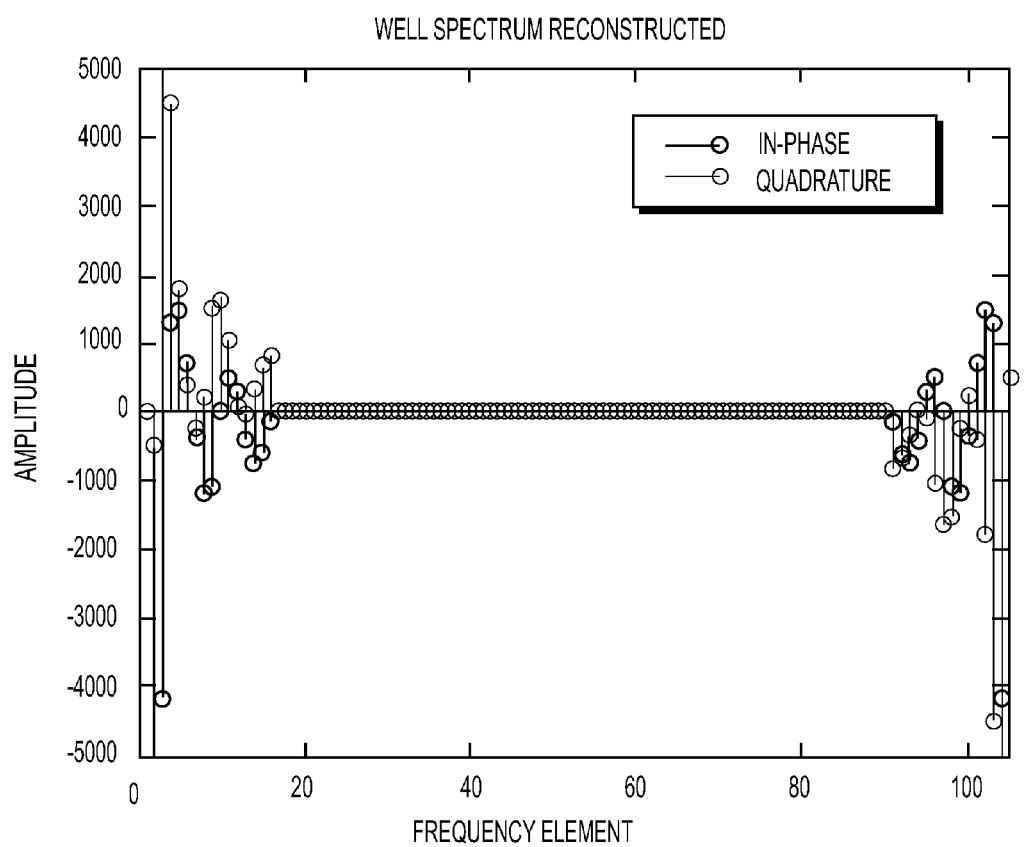
FIG. 15 depicts a reconstructed well spectrum, according to exemplary embodiments of the present disclosure.

FIG. 15 depicts a reconstructed well spectrum, according to exemplary embodiments of the present disclosure. For each well in a sensor array, a well spectrum may be reconstructed. A total number of reconstructed spectrum samples may be set to equal a number of time samples. Then, a positive low frequency complex spectrum may be constructed from the delta values multiplied by scale values, with the key frame added. DC and positive high frequency values may be zero, and negative frequency components may be constructed from the mirrored complex conjugate of the positive spectrum.

Figure 16:
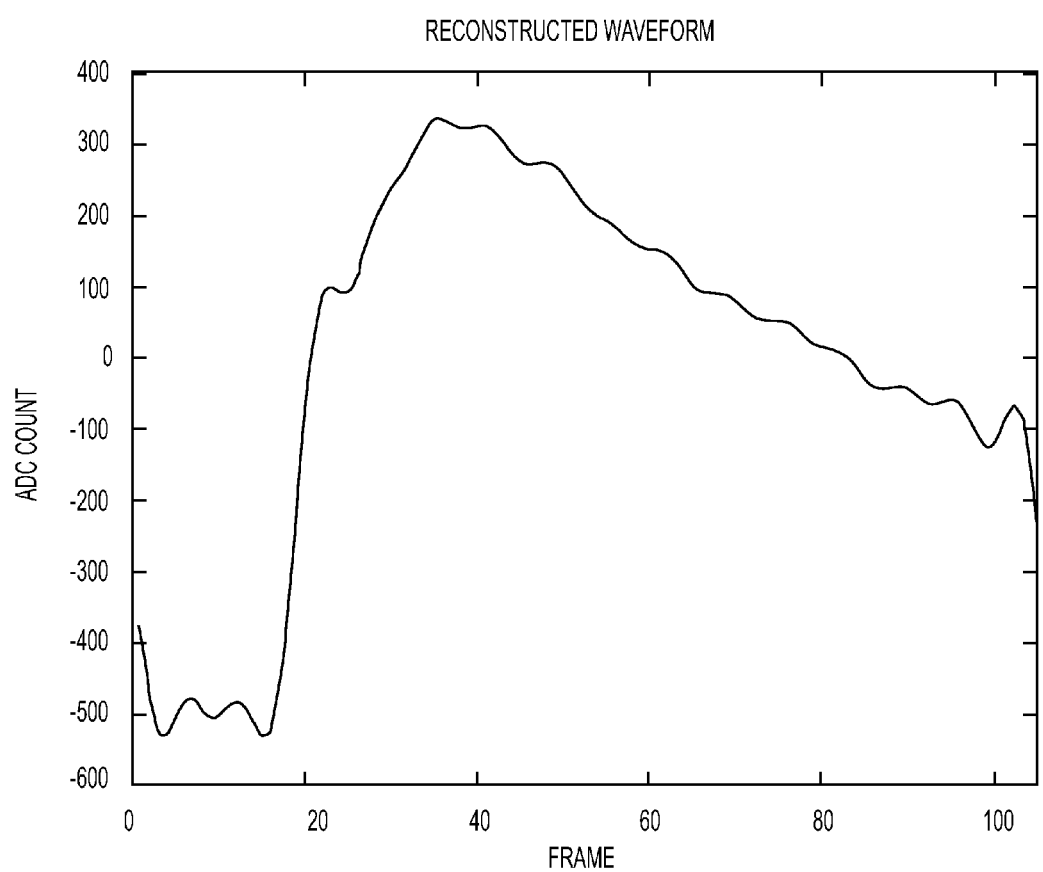
FIG. 16 depicts a reconstructed time-domain waveform, according to exemplary embodiments of the present disclosure.

FIG. 16 depicts a reconstructed time-domain waveform, according to exemplary embodiments of the present disclosure. After constructing the well spectrum for each of the wells in a sensor array, the frequency-domain spectrum may be converted to a time-domain waveform using an inverse integral transform. For example, an inverse Fourier transform may convert the reconstructed frequency-domain spectrum back to time-domain waveform. As mentioned above, the time-domain waveform may be pure real and has zero mean. The offset may be introduced by setting a DC frequency element to a non-zero value before applying Inverse Fourier Transform. The DC frequency value may be the offset divided by the number of samples and may be pure-real (no complex component).

In an example embodiment, an ISFET's data at 105 samples/flow from a prototype chip in development for the Ion Proton™ system for next-generation sequencing was reconstructed after being compressed to 25 frequency elements with minBits equal to three (3), maxBits equal to nine (9), across 440 flows. A 50 by 50 group of wells of the sensor array achieved an average compression of 27.69 bytes per well per flow. FIGS. 17A-17J depict exemplary raw time-domain waves and reconstructed time-domain waveforms of various wells of a sensor array, according embodiments of the present disclosure. As can be seen in FIGS. 17A-17J, the raw waveforms and reconstructed waveforms are nearly indistinguishable in most cases.

An example of source code for testing a compression ratio of a compression of sequencing data is provided below:

```
% Function to test the DFC compression algorithm on a single flow
function [data, raw, compressionRatio, bytesPerWell] =
testFlowDFC (fileName, patchWidth , patchHeight, maxBits, freqPts ,
wellUdx)
idxVal = 11:60;
% load thumbnail data
[img,ftimes] = Loadimage(fileName, [0 0 patchHeight patchWidth]);
analysisRegion = img(1:patchHeight,1:patchWidth,:);   % extract 50×50
                                                      % block to
                                                      compress
timePts = size(anal ysisRegion, 3); % expecting 105 frames per well
rawData = reshape(analysisRegion,patchWidth*patchHeight,timePts).';
% compress data
[keyframe, bitsPerFreq, scale, deltas, badIdx] = DFCompress(rawData,
freqPts, maxBits);
% Calculate compression ratio
rawDataSize = size(rawData,1) * size(rawData,2) * 2;  % unpacked bytes
keyframeSize = freqPts * 4 ;                          % 16-bit I +
                                                      16- bit Q
bitsPerFreqSize = freqPts * 0.5;                      % 4-bit nibble per
                                                      frequency point
scaleVecSize = length(scale) * 4;                     % 16- bit I + 16-bit Q scale
                                                      % per non-zero bitsPerFreq
                                                      point
deltaSize = (sum(bitsPerFreq) / 4) * size(rawData,2); % packed bytes
compDataSize = keyframeSize + bitsPerFreqSize + scaleVecSize +
deltaSize;
compressionRatio = rawDataSize / compDataSize ;
bytesPerWell = compDataSize / size(rawData,2);
% Reconstruct data
[reconData] = DFExpand(keyframe , bitsPerFreq, scale, deltas , timePts);
% Generate offset-removed raw data for comparison
offsetData = zeros(size(rawData)); % pre-allocate
for idx = 1:size(rawData,2)
    tmp = fft(rawData(:,idx));
    tmp(1) = 0 ; % remove DC offset
        offsetData(:,idx) = ifft(tmp);
    end
% Extract data for further analysis
data = reconData(idxVal, wellIdx);
raw = offsetData(idxVal , wellIdx);
```

Another example of source code for testing a compression ratio of a compression of sequencing data is provided below:

```
% Test the DFCcompression algorithm on a full run, extracting all the desired
% statistics.
function [data, raw, compressionRatio, bytesPerWell] =
testFullDFC(dataPath, flows , patchWidth, patchHeight, maxBits, freqPts ,
wellIdx, showMovie)

% pre-allocate buffers
data = zeros(50, flows);
raw = zeros(50, flows);
compressionRatio = zeros(1, flows);
bytesPerWell = zeros(1, flows);

h = waitbar(0,['Processing flow 0/',num2str(flows)]);

for idx = 1:flows
    fileName = [dataPath, sprintf('/acq_%04d.dat',(idx-1))];
    [data(:,idx), raw(:,idx), compressionRatio(idx), bytesPerWell(idx)] =
testFlowDFC(fileName, patchWidth, patchHeight, maxBits, freqPts, wellIdx);
    waitbar(idx/flows, h, ['Processing flow', num2str (idx),'/',num2str(flows)]);
end close(h);

fprintf('%.2f bytes per well\n', mean(bytesPerWell));

% plot traces
ymax=max([max(max(abs(raw)));max(max(abs(data)))])*1.1;
h = figure('position',[0 0 2000 1600]);
set(h,'PaperUnits','inches','PaperPosition', [0 0 20 16])
for figIdx=1:(flows/20)
    for y=1:4
        for x=1:5
            subplot(4,5,x+(y-1)*5) ;
            plot(11:60, raw(:,x+(y-1)*5+(figIdx-1)*20), 'r'); hold on;
            plot(11:60, data(:,x+(y-1)*5+(figIdx-1)*20), 'b'); hold off;
            legend('Raw','DFC','location','southeast');
            xlim([10 60]); ylim([-ymax ymax]);
            title(['Flow ', num2str(x+(y-1)*5+(figIdx-1)*20)]);
        end
    end
    drawnow;
    fname =
sprintf('Well_%d_%dpts_%dbit_flows_%d_to_%d.png',wellIdx,freqPts,maxBits,
(figIdx-1)*20+1,figIdx*20);
    print(h, '-dpng', '-r100', fname);
end
```

```
    close (h) ;

% generate "movie"
if exist('showMovie', 'var')
    h = figure( );
    for idx=1:flows
        figure(h);
        plot(11:60,[data(:,idx),raw(:,idx)]);
        ylim([-ymax ymax]);
        title(['Well ', num2str(wellIdx), ', ', num2str(freqPts), 'pts, ',
num2str(maxBits), 'bit limit (flow ', num2str(idx), ')']);
        drawnow;
        pause(0.5);
    end
end
```

Figure 18A:
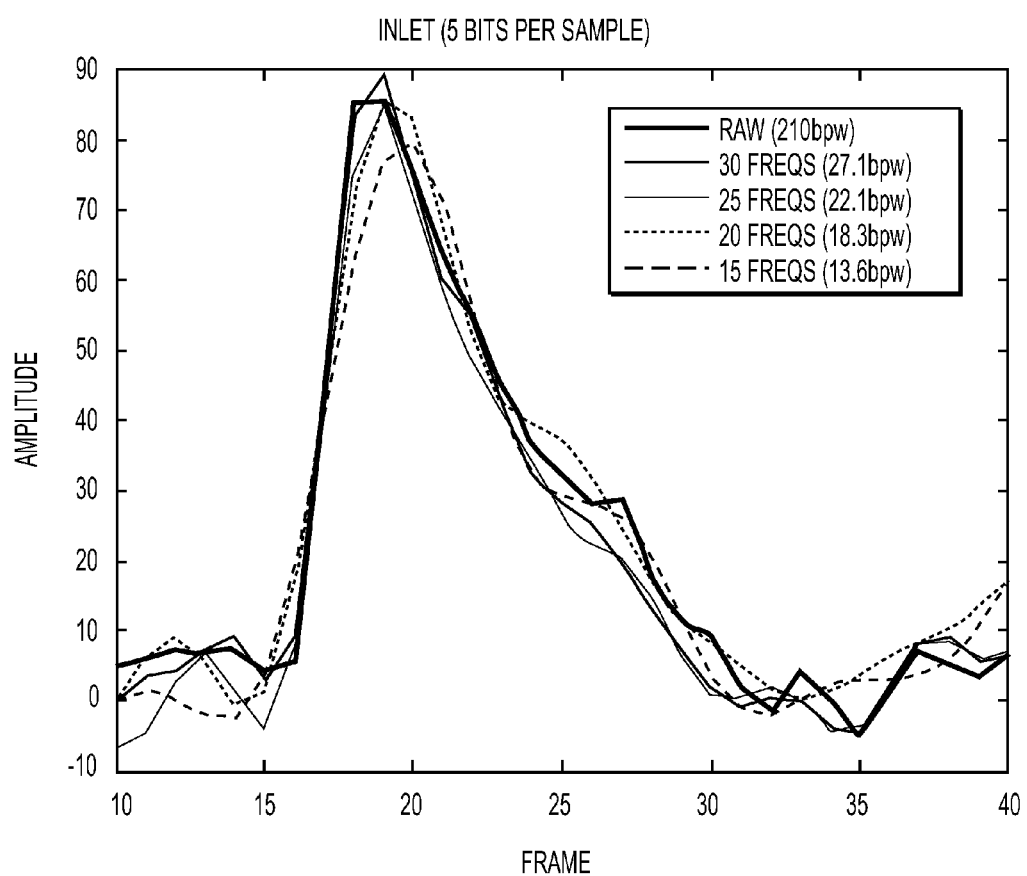
FIGS. 18A and 18B depict comparisons of exemplary incorporation peaks extracted from reconstructed data near an inlet, according to exemplary embodiments of the present disclosure.
Figure 18B:
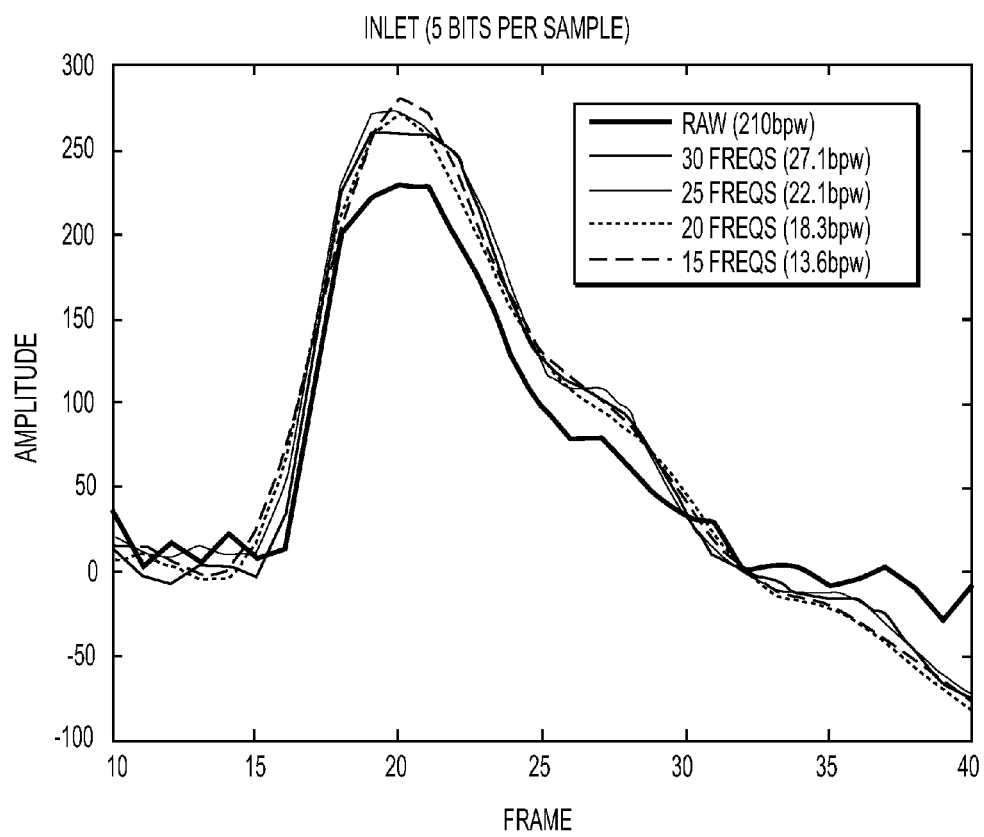

FIGS. 18A and 18B depict comparisons of exemplary incorporation peaks extracted from reconstructed data near an inlet, according to exemplary embodiments of the present disclosure. As shown in FIGS. 18A and 18B, differences between the raw waveform and the reconstructed waveforms compressed with different frequency elements may be larger where the rise time is sharpest and has significant information content at higher frequencies. Also as shown in FIGS. 18A and 18B, the more accurate reconstructed waveforms when compared to the raw waveform may be produced when more frequency components are used, which in turn reduces the compression ratio.

According to embodiments of the present disclosure, approximately 20% to 25% of the frequency elements may be required for high quality sequencing (e.g., less than 1% throughput drop compared to uncompressed data). Additionally, in embodiments of the present disclosure, the maxBits value may be at least 7 bits, which may ensure a sufficient dynamic range for accurate reconstruction. In one embodiment of the present disclosure, encoding of data of 105 frames may be achieved with 25 frequency elements having 8 bits maximum per sample. Thus, a compression of 221.5 bits per well per flow, average across 440 flows (approximately 7.5× from 16-bit raw) may be achieved, with minimal loss in AQ17 or AQ20 sequencing performance.

Figure 19A:
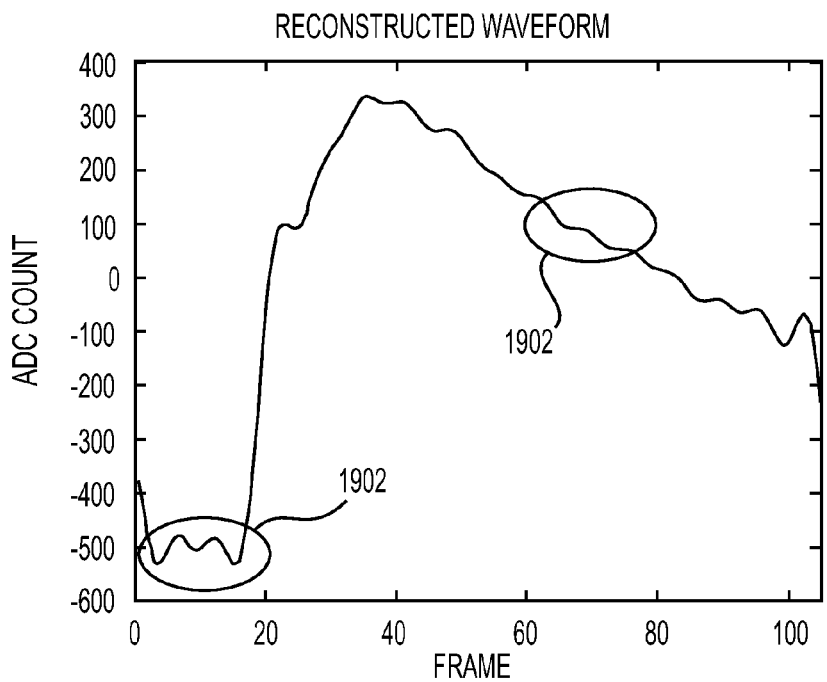
FIG. 19A depicts a reconstructed waveform, according to exemplary embodiments of the present disclosure.
Figure 19B:
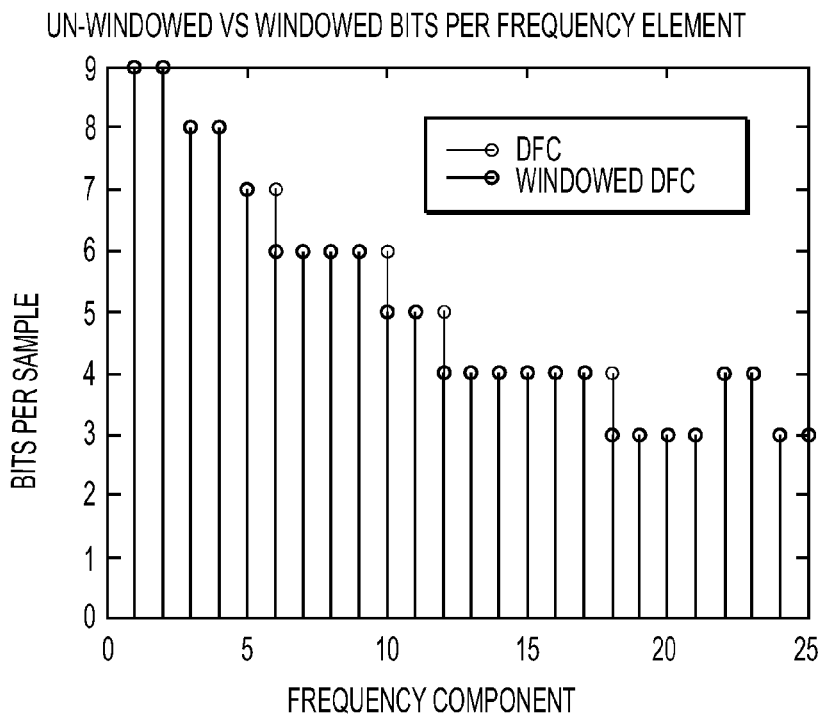
FIG. 19B depicts un-windowed bits per frequency element versus windowed bits per frequency element, according to exemplary embodiments of the present disclosure.

FIG. 19A depicts a reconstructed waveform, according to exemplary embodiments of the present disclosure. As shown in FIG. 19A, the reconstructed waveform may have "wobbles" 1902 caused by a raw waveform not starting at a zero value. The wobble may introduce a systematic residual error into the reconstructed waveform data. FIG. 19B depicts un-windowed bits per frequency element versus windowed bits per frequency element, according to exemplary embodiments of the present disclosure. In one embodiment of the present disclosure, a tapering window may be applied as a scaling vector to a DC-removed raw waveform before using an integral transform, such as a Fourier transform. An inverse of the tapering window may then be applied to the reconstructed data after the inverse integral transform, such as an inverse Fourier transform.

Figure 20:
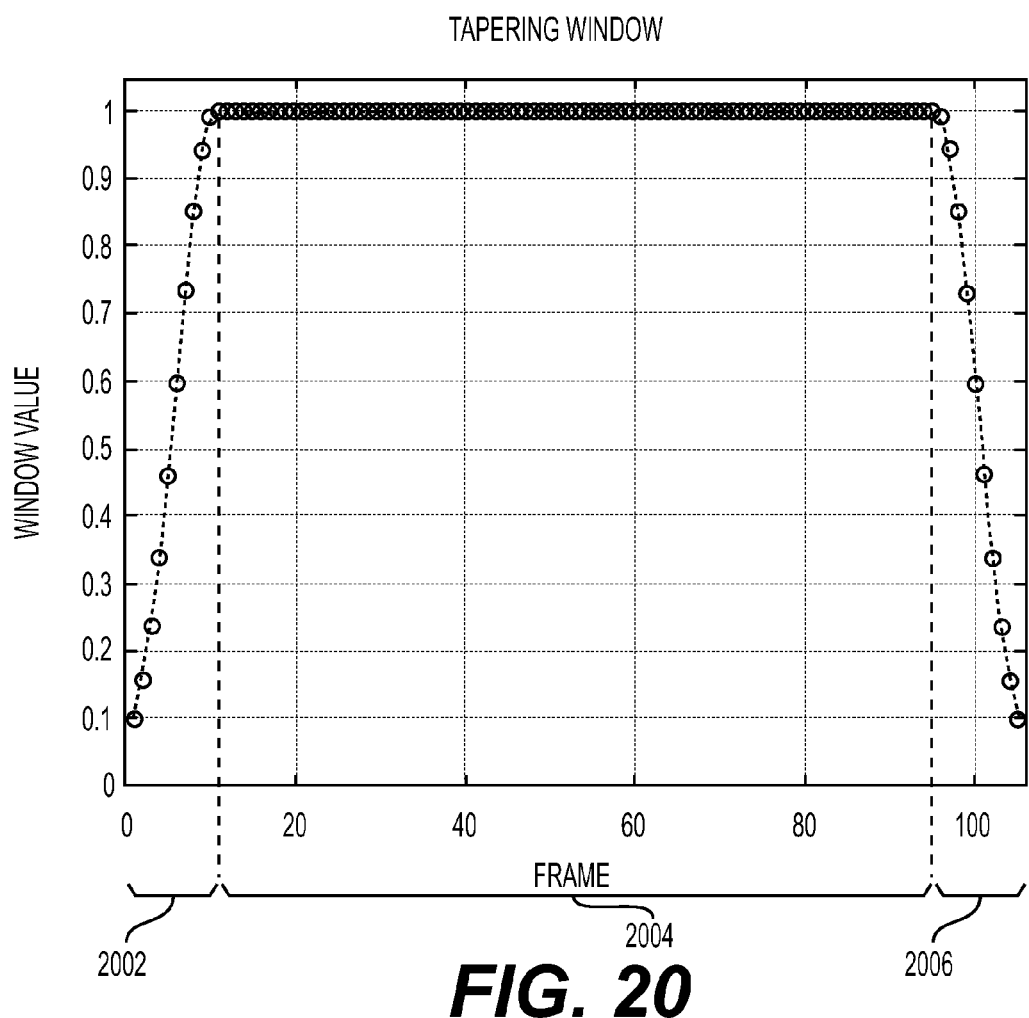
FIG. 20 depicts a tapering window, according to exemplary embodiments of the present disclosure.

FIG. 20 depicts a tapering window, according to exemplary embodiments of the present disclosure. The tapering window, as shown in FIG. 20, may include three sections: a front ramp 2002, a middle section 2004, and a tail ramp 2006. In an example embodiment, the front ramp 2002 and the tail ramp 2006 may be halves of an even length Gaussian window. A length and a curvature of the ramps may be configurable. In one embodiment, the curvature may be controlled by a Gaussian parameter "alpha." In the example embodiment, the middle section may be a "unity gain," where no change may be made to the raw waveform data.

Figure 21:
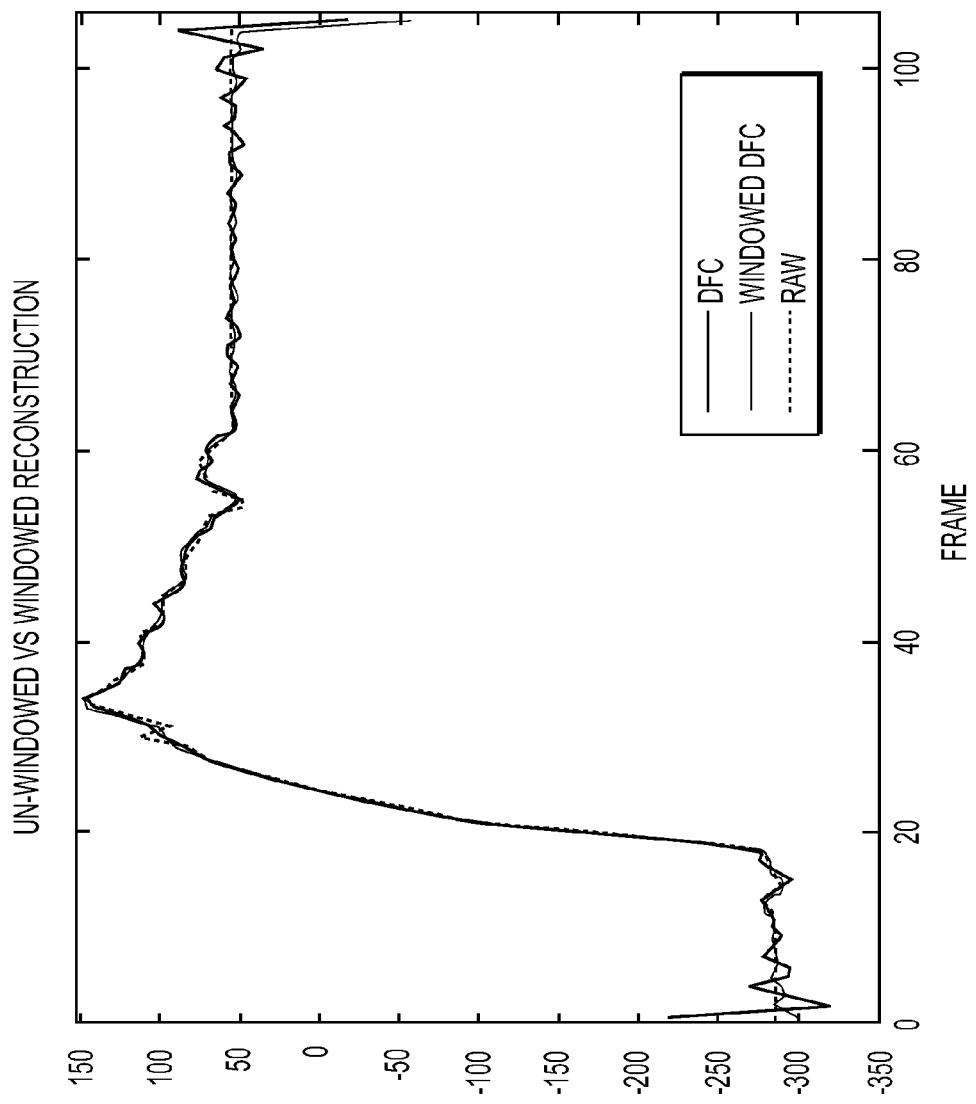
FIG. 21 depicts an un-windowed reconstructed waveform versus a windowed reconstructed waveform, according to exemplary embodiments of the present disclosure.

FIG. 21 depicts an un-windowed reconstructed waveform versus a windowed reconstructed waveform, according to exemplary embodiments of the present disclosure. As shown in FIG. 21, the wobble may be noticeably reduced through the use of a tapering window. Compression may be improved for equivalent sequencing performance when compared to un-windowed data. A shorter window length may also achieve better results. In one example embodiment, the first five (5) frames and the last five (5) frames were used for the ramping transitions. In the example embodiment, an optimum "alpha" parameter may be about 2.0+/−15% to about 2.3+/−15% (the Gaussian window equation used to generate the front/tail ramps). In a particular embodiment, the optimum "alpha" parameter may be about 2.15+/−15%. In the exemplary embodiment, AQ47 performance may be improved over un-windowed results.

An example of source code for a tapering window used a compression of sequencing data is provided in the ASCII text file named LT00869_Computer_Program_Listing.txt, referenced above. The source code includes instructions for generating the new window coefficients, generating a set of Gaussian window coefficients, lossy compression of the data, and reconstructing the data from the compressed frequency domain vectors.

Sequencing aspects relating to the present disclosure may comprise one or more features described in Rothberg et al., U.S. Pat. No. 7,948,015, and Rothberg et al., U.S. Patent Application Publication Nos. 2010/0137143, 2009/0026082, and 2010/0282617, which are all incorporated by reference herein in their entirety.

Data analysis aspects relating to the present disclosure (e.g., processing of measurements, generation of predicted signals and modeling residuals using a phasing model, calling of bases, etc.) may comprise one or more features described in Davey et al., U.S. Patent Application Publication No. 2012/0109598, and Sikora et al., U.S. Patent Application Publication Nos. 2013/0060482 and 2013/0090860, which are all incorporated by reference herein in their entirety.

In various embodiments, one or more aspects of the foregoing methods may be implemented at least in part using a field programmable gate array ("FPGA") technology and/or graphics processing unit ("GPU"). The following documents are all incorporated by reference herein in their entirety: Woods, R., et al., *FPGA-based Implementation of Signal Processing Systems*, John Wiley & Sons (2008); Gallagher, S., *Mapping DSP Algorithms Into FPGAs*, Xilinx, Inc., available at http://www.ieee.li/pdf/viewgraphs/ mapping_dsp_algorithms_into_fpgas.pdf; and Bartholomä, R., et al., *Implementing Signal Processing Algorithms on FPGAs*, University of Applied Sciences Pforzheim, Germany, available at http://citeseerx.ist.psu.edu/viewdoc/download?doi=10.1.1.130.8731&rep=rep1&type=pdf.

Figure 22:
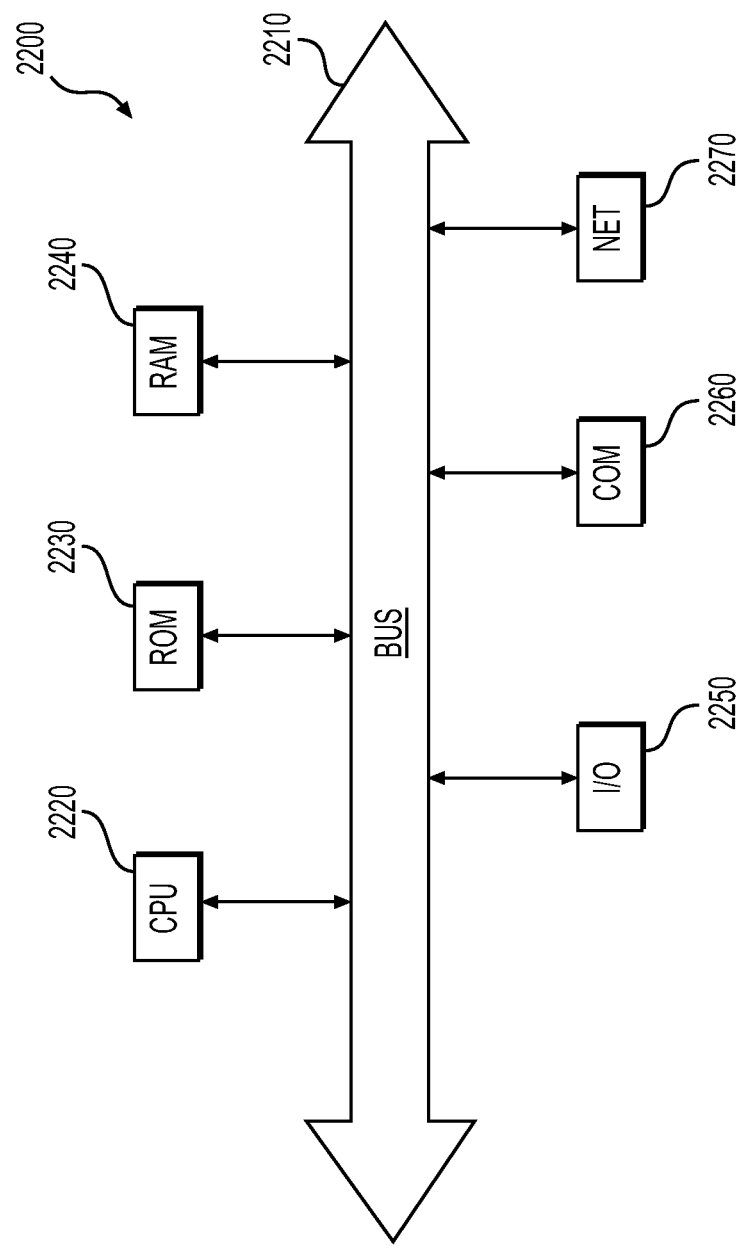
FIG. 22 is a simplified functional block diagram of a computer that may be configured as a computer, system, and/or server for executing the methods, according to exemplary embodiments of the present disclosure.

FIG. 22 is a simplified functional block diagram of a computer that may be configured as a computer, system, and/or server for executing the methods described above, according to an exemplary embodiment of the present disclosure. Specifically, in one embodiment, as shown in FIG. 22, any of computers, systems, and/or servers implementing the above-described disclosure may be an assembly of hardware 2200 including, for example, a data communication interface 2260 for packet data communication. The platform may also include a central processing unit ("CPU") 2220, in the form of one or more processors, for executing program instructions. The platform typically includes an internal communication bus 2210, program storage, and data storage for various data files to be processed and/or communicated by the platform such as ROM 2230 and RAM 2240, although the system 2200 often receives programming and data via network communications 2270. The server 2200 also may include input and output ports 2250 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the presently disclosed application, methods, computers, servers, devices, and systems are described with exemplary reference to computer applications and to transmitting various types of data, it should be appreciated that the presently disclosed embodiments may be applicable to any environment, such as a desktop or laptop computer, etc. Also, the presently disclosed embodiments may be applicable to any type of Internet protocol that is equivalent or successor to HTTP.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

The example of source code for compression of sequencing data is provided below:

```
function [keyframe, bitsPerFreq, scale, deltas, badIdx] = DFCompress(rawData,
freqPts, maxBits)
    % Step 1 - convert to frequency domain
    tmp = zeros (size(rawData)); % pre-allocate
    for idx = 1:size(rawData,2)
        tmp(:,idx) = fft(rawData(:,idx));
    end
    % Step 2 - discard DC and negative frequency components, since DC and
    % negative frequency components are just the complex conjugate of the positive
    % frequencies. Only keep the first specified number of frequency samples.
    freqData = tmp(2:(freqPts+1),:);
    % Step 3 - generate key frame and correlation statistics
    keyframe = zeros(1,size(freqData,1)); % pre-allocate
    for idx = 1 : 3izc(frcqDntn, l)
        keyframe(idx) = mean(freqData(idx,:));
    end
    corrKnl = keyframe'; % use complex conjugate as correlation kernel
    corrVal = zeros(1,size(freqData,2)); % pre-allocate
    z = zeros(size(freqData)); % pre- allocate
    for idx = 1:size(freqData,2)
        corrVal(idx) = freqData(:,idx).' * corrKnl; % correlate wells
        z(:,idx) = freqData(:,idx) .* corrKnl; % correlate frequency components
    end
    corrNorm = corrVal ./ (keyframe*corrKnl); %normalize
    badidx = find(abs(corrNorm) < (1-std(abs(corrNorm)))); %identify bad wells
    avgMag = zeros(1,size(freqData,1)); % pre-allocate
    sdMag = zeros(1,size(freqData,1)); % pre-allocate
    sdAng = zeros(1,size(freqData,1)); % pre-allocate
    for idx = 1:size(freqData,1)
        avgMag(idx) = mean(abs(z(idx,:)));
        sdMag(idx) = std(abs(z(idx,:)));
        sdAng(idx) = std(angle(z(idx,:)));
    end
```

-continued

```
% Step 4 - Estimate the entropy of each frequency point and convert to bits per
% sample (data is complex , so total number of bits will be double)
% Total number of bits is sign + (maxBits-1) 2's complement magnitude
% The first three samples will usually be zero, since (generally speaking) they
% only contain information relevant to the background pH step.
rawEmphasis = (sdAng .* sdMag) ./ avgMag;
emphasis= rawEmphasis ./ max(rawEmphasis); % normalize
bitsPerFreq = round((maxBits-1)+log2(emphasis)); % magnitude bits per value
bitsPerFreq(find(bitsPerFreq < 2)) = 2 ; % constrain minimum number of bits
bitsPerFreq = bitsPerFreq + 1 ; % add sign bit
% Step 5 - calculate raw spectrum delta values and scaling parameters for
% non- zero bitsPerFreq frequencies
encIdx = 1;
bitsPerFreqIdx = find(bitsPerFreq) ;
rawDelta = zeros(length(bitsPerFreqIdx),size(freqData,2)); % pre-allocate
deltaRange = zeros(1,length(bitsPerFreqIdx)); % pre-allocate
scale= zeros(1,length(bitsPerFreqIdx)); % pre-allocate
for idx = bitsPerFreqIdx
    rawDelta(encIdx,:) = freqData(idx,:) - keyframe(idx);
    tmpReal = max(abs([max(real(rawDelta(encIdx,:))), min(real(rawDelta(encIdx,:)))]));
    tmpImag = max(abs([max(imag(rawDelta(encIdx,:))), min(imng(rawDelta(encIdx,:)))]));
    deltaRange(encIdx) = tmpReal + 1i*tmpImag;
    scale(encIdx) = deltaRange(encIdx)/((2^(bitsPerFreq(idx)-1))-1);
    encIdx = encIdx + 1;
end
% Step 6 - Quantize spectrum delta values and clip values at min/max limits
deltas = zeros(size(rawDelta)); % pre-allocate
for idx = 1:size(rawDelta,1)
    deltas (idx,:) = round((real(rawDelta(idx,:))/real(scale(idx)))+1i*(imag(rawDelta(idx,:))/imag(scale(idx)))) ;
end
% Step 7 - Bit-packing based on bitsPerFreq.
```

What is claimed is:

1. A computer-implemented method for compression of sequencing data, the method comprising:
   receiving waveform data associated with a chemical event occurring on a sensor array, the waveform data including a plurality of time-based waveforms of a corresponding plurality of locations of the sensor array;
   converting, by at least one processor, each time-based waveform of the waveform data into a frequency-domain spectrum;
   generating, by the at least one processor, a key frame based on a plurality of the frequency-domain spectrums;
   calculating, by the at least one processor, an entropy value for each frequency element based on a phase angle standard deviation and a magnitude standard deviation corresponding to each frequency element of the plurality of the frequency-domain spectrums;
   calculating, by the at least one processor, for each of the frequency-domain spectrums, a difference between the frequency-domain spectrum and the key frame to form frequency delta values corresponding to each frequency-domain spectrum;
   encoding, by the at least one processor, the frequency delta values to form encoded frequency delta values;
   packing, by the at least one processor, the encoded frequency delta values to form a packed data structure; and
   storing, by the at least one processor, the packed data structure in a memory.

2. The method of claim 1, wherein converting each time-based waveform of the waveform data into a frequency-domain spectrum includes:
   transforming, by the at least one processor, each time-based waveform of the waveform data into the frequency-domain spectrum using an integral transform.

3. The method of claim 1, wherein generating the key frame based on a plurality of frequency-domain spectrums includes:
   averaging, by the at least one processor, the plurality of the frequency-domain spectrums.

4. The method of claim 1, further comprising:
   truncating, by the at least one processor, each of the plurality of the frequency-domain spectrums to form a plurality of truncated frequency-domain spectrums,
   wherein generating the key frame is based on the plurality of truncated frequency-domain spectrums.

5. The method of claim 1, further comprising:
   truncating, by the at least one processor, the key frame to form a truncated key frame; and
   truncating, by the at least one processor, each of the plurality of the frequency-domain spectrums to form a plurality of truncated frequency-domain spectrums,
   wherein calculating the difference between each frequency-domain spectrum and the key frame includes calculating the difference between each of the truncated frequency-domain spectrums and the truncated key frame.

6. The method of claim 1, further comprising:
   determining, by the at least one processor, a number of bits required to encode each frequency element of the frequency delta values based on the entropy value for each frequency element.

7. The method of claim 6, further comprising:
   calculating, by the at least one processor, a scaling vector for the frequency delta values, the scaling vector being based on the determined number of bits required to encode each frequency element of the frequency delta values.

8. The method of claim 6, wherein storing the packed data structure further comprises:
storing, by the at least one processor, the number of bits required to encode each frequency element in a bits-per-element vector in a header, wherein the header corresponds to the packed data structure for at least a portion of the sensor array.

9. The method of claim 1, wherein storing the packed data structure further comprises:
storing, by the at least one processor, the key frame in a header, wherein the header corresponds to the packed data structure for at least a portion of the sensor array.

10. A system for compression of sequencing data, the system comprising:
a data storage device that stores instructions for compression of sequencing data; and
a processor configured to execute the instructions to perform a method including:
receiving waveform data associated with a chemical event occurring on a sensor array, the waveform data including a plurality of time-based waveforms of a corresponding plurality of locations of the sensor array;
converting each time-based waveform of the waveform data into a frequency-domain spectrum;
generating a key frame based on a plurality of the frequency-domain spectrums;
calculating an entropy value for each frequency element based on a phase angle standard deviation and a magnitude standard deviation corresponding to each frequency element of the plurality of the frequency-domain spectrums;
calculating, for each of the frequency-domain spectrums, a difference between the frequency-domain spectrum and the key frame to form frequency delta values corresponding to each frequency-domain spectrum;
encoding the frequency delta values to form encoded frequency delta values;
packing the encoded frequency delta values to form a packed data structure; and
storing the packed data structure in a memory.

11. The system of claim 10, wherein converting each time-based waveform of the waveform data into a frequency-domain spectrum includes:
transforming each time-based waveform of the waveform data into the frequency-domain spectrum using an integral transform.

12. The system of claim 10, wherein generating the key frame based on a plurality of frequency-domain spectrums includes:
averaging the plurality of the frequency-domain spectrums.

13. The system of claim 10, wherein the processor is further configured to execute the instructions to perform the method further including:
truncating each of the plurality of the frequency-domain spectrums to form a plurality of truncated frequency-domain spectrums,
wherein generating the key frame is based on the plurality of truncated frequency-domain spectrums.

14. The system of claim 10, wherein the processor is further configured to execute the instructions to perform the method further including:

truncating the key frame to form a truncated key frame; and
truncating each of the plurality of the frequency-domain spectrums to form a plurality of truncated frequency-domain spectrums,
wherein calculating the difference between each frequency-domain spectrum and the key frame includes calculating the difference between each of the truncated frequency-domain spectrums and the truncated key frame.

15. The system of claim 10, wherein the processor is further configured to execute the instructions to perform the method further including:
determining a number of bits required to encode each frequency element of the frequency delta values based on the entropy value for each frequency element.

16. The system of claim 15, wherein the processor is further configured to execute the instructions to perform the method further including:
calculating a scaling vector for the frequency delta values, the scaling vector being based on the determined number of bits required to encode each frequency element of the frequency delta values.

17. The system of claim 15, wherein the processor is further configured to execute the instructions to perform the method, wherein storing the packed data structure further comprises:
storing the number of bits required to encode each frequency element in a bits-per-element vector in the header, wherein the header corresponds to the packed data structure for at least a portion of the sensor array.

18. The system of claim 10, wherein the processor is further configured to execute the instructions to perform the method, wherein storing the packed data structure further comprises:
storing the key frame in a header, wherein the header corresponds to the packed data structure for at least a portion of the sensor array.

19. A non-transitory computer-readable medium storing instructions that, when executed by a computer, cause the computer to perform a method for compression of sequencing data, the method including:
receiving waveform data associated with a chemical event occurring on a sensor array, the waveform data including a plurality of time-based waveforms of a corresponding plurality of locations of the sensor array;
converting, by at least one processor, each time-based waveform of the waveform data into a frequency-domain spectrum;
generating, by the at least one processor, a key frame based on a plurality of the frequency-domain spectrums;
calculating, by the at least one processor, an entropy value for each frequency element based on a phase angle standard deviation and a magnitude standard deviation corresponding to each frequency element of the plurality of the frequency-domain spectrums;
calculating, by the at least one processor, for each of the frequency-domain spectrums, a difference between the frequency-domain spectrum and the key frame to form frequency delta values corresponding to each frequency-domain spectrum;
encoding, by the at least one processor, the frequency delta values to form encoded frequency delta values;
packing, by the at least one processor, the encoded frequency delta values to form a packed data structure; and storing, by the at least one processor, the packed data structure in a memory.

20. The computer-readable medium of claim 19, wherein storing the packed data structure further comprises:
storing, by the at least one processor, the key frame in a header, wherein the header corresponds to the packed data structure for at least a portion of the sensor array.

* * * * *